United States Patent [19]

Feit et al.

[11] 4,082,851
[45] Apr. 4, 1978

[54] SULPHONAMIDES, COMPOSITIONS CONTAINING THE SAME AND METHODS FOR USING THE SAME IN THE TREATMENT OF HYPERTENSION OR ODEMEAS

[75] Inventors: Peter Werner Feit, Gentofte; Ole Bent Tvaermose Nielsen, Vanlose; Herta Bruun, Malov; Claus Aage Svensgaard Bretting, Copenhagen, all of Denmark

[73] Assignee: Leo Pharmaceutical Products Ltd., Ballerup, Denmark

[21] Appl. No.: 696,547

[22] Filed: Jun. 16, 1976

[30] Foreign Application Priority Data

Jul. 8, 1975    United Kingdom .............. 28770/75
Jul. 8, 1975    United Kingdom .............. 28775/75
Jul. 8, 1975    United Kingdom .............. 28774/75
Jul. 8, 1975    United Kingdom .............. 28773/75
Jul. 8, 1975    United Kingdom .............. 28772/75

[51] Int. Cl.² .................. A61K 31/18; A61K 31/135; C07C 143/80; C07C 143/78
[52] U.S. Cl. .......................... 424/300; 260/239 BE; 424/275; 424/317; 424/321; 260/250 A; 260/250 B; 260/256.5 R; 260/293.73; 260/294.8 F; 260/302 R; 260/302 D; 260/307 R; 260/326.82; 260/332.3 R; 260/333; 260/347.2; 260/501.19; 260/501.21; 260/556 AR; 260/556 B; 260/566 A; 424/244; 424/246; 424/250; 424/251; 424/263; 544/3; 424/267; 544/63; 424/270; 548/300; 548/373; 424/272; 560/9; 424/274
[58] Field of Search ............ 260/470, 556 AR, 556 B, 260/501.19, 501.21; 424/300, 321, 304, 317

[56] References Cited

U.S. PATENT DOCUMENTS

| | | | |
|---|---|---|---|
| 2,871,233 | 1/1959 | Pfitzner et al. | 260/556 B X |
| 3,565,920 | 2/1971 | Werner | 260/556 B X |
| 3,565,952 | 2/1971 | Liebenow | 260/556 B |
| 3,706,790 | 12/1972 | Sprague et al. | 260/556 AR X |
| 3,806,534 | 4/1974 | Feit | 260/556 B X |
| 3,806,542 | 4/1974 | Werner | 260/556 B X |
| 3,816,482 | 6/1974 | Feit et al. | 260/518 R X |
| 3,860,647 | 1/1975 | Colella et al. | 260/556 AR |
| 3,950,380 | 4/1976 | Feit et al. | 260/465 D |

Primary Examiner—Daniel E. Wyman
Assistant Examiner—Thomas A. Waltz
Attorney, Agent, or Firm—Cushman, Darby & Cushman

[57] ABSTRACT

The invention relates to a series of new compounds, salts thereof and to methods for the preparation of the compounds which have the general formula

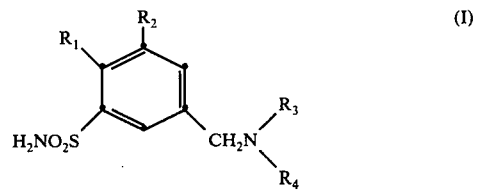

in which
  $R_1$ stands for an unsubstituted or substituted phenoxy, phenylthio, benzyl, phenylsulfinyl, or anilino radical;
  $R_2$ stands for a $-YR_2'$ radical, in which Y represents $-O-$, $-S-$, or $-NH-$, and $R_2'$ represents $C_1$-$C_6$-alkyl, $C_2$-$C_6$-alkenyl or -alkynyl; or methyl or ethyl substituted with phenyl, furyl, thienyl or pyridyl;
  $R_3$ and $R_4$ which can be the same or different, and unsubstituted or substituted, stand for hydrogen or for a straight or branched $C_1$-$C_8$-alkyl, $C_2$-$C_8$-alkenyl or -alkynyl radical, a $C_5$-$C_7$-cycloalkyl, a phenyl, or a 5-, 6- or 7-membered heterocyclic ring system containing not more than two hetero atoms selected from the group consisting of oxygen, sulphur and nitrogen, or for a $C_1$-$C_3$ alkyl radical substituted with phenyl or with a 5-, 6- or 7-membered heterocyclic ring system containing not more than two hetero atoms selected from the group consisting of oxygen, sulphur and nitrogen; and
  $R_4$ furthermore stands for a lower carbalkoxy radical, a $C_1$-$C_6$ alkanoyl radical, or a benzoyl radical; and salts thereof with pharmaceutically acceptable acids.

The compounds of the invention possess a pronounced diuretic and/or saluretic activity with a very low excretion of potassium ions. The low toxicity also makes the present compounds particularly valuable in human and veterinary practice.

28 Claims, No Drawings

SULPHONAMIDES, COMPOSITIONS CONTAINING THE SAME AND METHODS FOR USING THE SAME IN THE TREATMENT OF HYPERTENSION OR ODEMEAS

This invention relates to a series of new compounds, salts thereof and to methods for the preparation of the compounds which are valuable in the human and veterinary practice and have the general formula

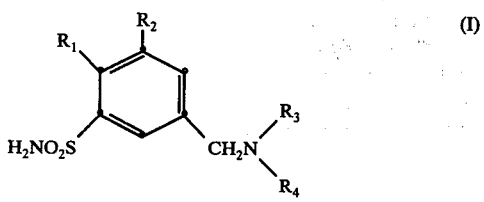

in which $R_1$ stands for an unsubstituted or substituted phenoxy, phenylthio, benzyl, phenylsulfinyl, or anilino radical;

$R_2$ stands for a $-YR_2'$ radical, in which Y represents $-O-$, $-S-$, or $-NH-$, and $R_2'$ represents $C_1-C_6$-alkyl, $C_2-C_6$-alkenyl or -alkynyl; or methyl or ethyl substituted with phenyl, furyl, thienyl or pyridyl;

$R_3$ and $R_4$ which can be the same or different, and unsubstituted or substituted, stand for hydrogen or for a straight or branched $C_1-C_8$-alkyl, $C_2-C_8$-alkenyl or -alkynyl radical, a $C_5-C_7$-cycloalkyl, a phenyl, or a 5-, 6- or 7-membered heterocyclic ring system containing not more than two hetero atoms selected from the group consisting of oxygen, sulphur and nitrogen, or for a $C_1-C_3$ alkyl radical substituted with phenyl or with a 5-, 6- or 7-membered heterocyclic ring system containing not more than two hetero atoms selected from the group consisting of oxygen, sulphur and nitrogen; and $R_4$ furthermore stands for a lower carbalkoxy radical, a $C_1-C_6$ alkanoyl radical, or a benzoyl radical; and salts thereof with pharmaceutically acceptable acids.

More specifically, $R_2'$ when representing an alkenyl or alkynyl radical, stands for a radical with three to five carbon atoms.

More specifically, $R_3$ and $R_4$ may each represent hydrogen, $C_1-C_8$ alkyl, $C_3-C_5$ -alkenyl, $C_5-C_7$ -cycloalkyl, phenyl, furyl, thienyl, morpholinyl, pyridyl, or $R_3$ and $R_4$ each represents $C_1-C_3$ alkyl substituted with one or two phenyl radicals or with furyl, tetrahydrofuryl, pyridyl and piperidyl, or $R_4$ represents carbethoxy, $C_2-C_4$ alkanoyl or benzoyl.

As examples of radicals falling within the above definitions and the definitions used in the present specification, mention may especially be made of:

Alkyl: methyl, ethyl, different isomers of propyl, butyl, pentyl, hexyl, heptyl, octyl;

cycloalkyl: cyclopentyl, cyclohexyl and cycloheptyl;

alkenyl: different isomers of propenyl, butenyl, pentenyl;

alkynyl: 1- and 2-propynyl;

heterocyclic radicals: furyl, thienyl, pyrrolidyl, pyrazolyl, pyrazolinyl, pyrazolidinyl, oxazolyl, thiazolyl, thiadiazolyl, pyridyl, piperidyl, tetrahydropyridazinyl, hexahydropyridazinyl, pyrimidyl, pyrazinyl, morpholinyl, thiazinyl, perhydroazepinyl, hexahydrooxepinyl.

The above substituents $R_1$, $R_2'$, $R_3$, and $R_4$ can be substituted in different positions with different groups, such as one or more halogen atoms, e.g. fluorine, chlorine or bromine atoms, lower alkyl, halo-lower alkyl, e.g. trifluoromethyl; nitro and amino groups, mono- or dialkylamino or acylamino groups, hydroxy groups, which may be etherified, e.g. lower alkoxy, such as methoxy, ethoxy, n-propoxy, isopropoxy, n-butoxy or isobutoxy, or esterified with lower aliphatic carboxylic acids, such as lower alkanoic acids, e.g. acetic, propionic or pivalic acid, lower alkenoic acids, e.g. acrylic or methacrylic acid, or with lower aliphatic dicarboxylic acids, e.g. oxalic, malonic, succinic, glutaric, adipic, maleic or fumaric acid or their acid esters with lower alkanols, e.g. methanol or ethanol; or etherified mercapto groups such as methylthio, ethylthio, isopropylthio, butylthio, isobutylthio or phenylthio radicals.

Whenever the expression "lower" is used in the foregoing and in the following in connection with an organic radical it indicates a content of from 1 to 6 carbon atoms.

The salts of the compounds of the invention are pharmaceutically acceptable salts, and include, for example, salts with non-toxic, pharmaceutically acceptable acids, such as hydrochloric and hydrobromic acid, phosphoric acid, nitric acid, p-toluenesulfonic acid, methanesulfonic acid, formic acid, acetic acid, propionic acid, citric acid, tartaric acid and maleic acid.

Of particular value are the following combinations of substituents:

a. Compounds of formula I in which $R_1$ stands for an unsubstituted or substituted phenoxy or phenylthio radical and Y stands for $-NH-$.

b. Compounds of formula I in which $R_1$ stands for an unsubstituted or substituted phenoxy or phenylthio radical and Y stands for $-S-$.

c. Compounds of formula I in which $R_1$ stands for an unsubstituted or substituted anilino radical and Y stands for $-NH-$.

d. Compounds of formula I in which $R_1$ stands for an unsubstituted or substituted benzyl radical and Y stands for $-NH-$.

e. Compounds of formula I in which $R_1$ stands for an unsubstituted or substituted benzyl radical and Y stands for $-O-$ or $-S-$.

It has been found that the compounds of the invention possess a pronounced diuretic and/or saluretic activity with a very low excretion of potassium ions. The low toxicity also makes the present compounds particularly valuable in human and veterinary practice.

Furthermore the compounds of the invention are capable of producing a great maximal natriuretic effect exceeding the thiazides and thiazide type diuretics in this respect. This is especially of importance in the treatment of patients with severe renal failure and/or severe cardiac insufficiency. The rational drugs used for this indication are ethacrynic acid, furosemide and bumetanide. These drugs are organic acids and therefore excreted by the organic acid secretory mechanism. The compounds of the invention are distinguished from these drugs by not being carboxylic acids and therefore do not complete neither with other acidic drugs like penicillin nor with naturally occurring acidic metabolites. This is of importance with respect to drug interaction due to a limited capacity of the acid secretory transport.

Japanese patent applications Nos. 45228/62 and 27746/63 describe a method for the preparation of chlorosulfamylbenzylamines, these compounds having value as intermediates, and, according to the Japanese specifications, possessing some diuretic effect when administered in rats. However, in the experiments performed in connection with the present invention, it was impossible to verify a useful diuretic effect when administering in doses of the same magnitude as used for the present compounds.

The present compounds are effective after oral, enteral or parenteral administration, and are preferably prescribed in the form of tablets, pills, dragees, or capsules containing a compound of formula I or a salt thereof as defined above, mixed with carriers and/or auxiliary agents.

Salts, which are soluble in water, can advantageously be administered by injection as aqueous solutions. The compounds of the invention are useful in the treatment of oedematous conditions, e.g. cardiac, hepatic, renal, and pulmonary oedema, and of pathological conditions which produce an abnormal retension of the electrolytes of the body, and in the treatment of hypertension.

In pharmaceutical compositions containing the compounds of the invention, organic or inorganic, solid or liquid carriers suitable for oral, enteral, or parenteral administration can be used to make up the composition. Gelatine, lactose, starch, magnesium stearate, talc, vegetable and animal fats and oils, gum, polyalkylene glycol, or other known carriers for medicaments are all suitable as carriers.

The pharmaceutical compositions can be prepared as slow-release formulations. It should, however, be noted that certain compounds of formula I in themselves show an advantageous prolonged diuretic effect.

In the pharmaceutical compositions, the proportion of therapeutically active material to carrier substances can vary between 0.5 percent and 90 percent.

The compositions may further contain other therapeutic compounds applied in the treatment of, for example oedemas and hypertension, besides the well-known auxiliary agents. Such other compounds can be, for instance β-adrenergic receptor blocking drugs e.g. propranolol or timolol, or other synthetic hypotensive compounds, e.g. hydralazine, or other diuretics and saluretics, such as the well-known benzothiadiazines and thiazide type diuretics, e.g. hydroflumethiazide and chlorthalidone; potassium-sparing diuretics, e.g. triamterene can also be used in the preparation of the compositions. It can also be desirable to add small amounts of aldosterone antagonists, e.g. spironolactone, or to combine the compounds of the invention with a slow-release formulation of a potassium salt. It has also been found that by combination of a compound with the general formula I with some of the therapeutic compounds as described above the activity of both compounds can be enhanced. In that manner a higher therapeutic effect is achieved with the combination than with either of the two compounds alone.

It is another object of the invention to provide a method of preparing the compounds of the invention.

The compounds of formula I can be prepared by different methods. In one method, a compound of the formula II

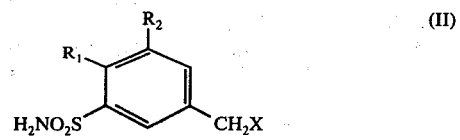

in which $R_1$ and $R_2$ have the meanings defined before, and X is capable of forming a "good leaving group", X thus standing for e.g. a halogen atom such as chlorine, bromine or iodine, an alkyl- or arylsulphonyloxy group, a chlorosulphonyloxy group, an alkylsulphate group, a hydrogensulphate group, an alkylsulphite group, a mono- or dialkylphosphate group, an alkylchloro-phosphate group or a nitrate group, is reacted with an amine

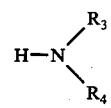

in which $R_3$ and $R_4$ have the meanings defined before, to form the desired compound of formula I.

The starting material of formula II can be prepared according to the following reaction scheme:

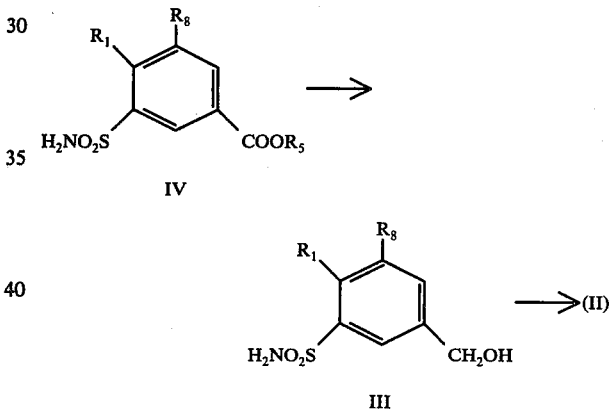

in which formulae $R_1$ has the above meanings, -COOR$_5$ indicates a carboxylic ester group, $R_5$ being, for instance, lower alkyl, and $R_8$ stands for $R_2$ or -YH. In case $R_8$ stands for -YH, the obtained compound of formula III is thereafter alkylated to form a compound of formula III, in which $R_8$ stands for $R_2$.

The compounds of formula IV are known (for instance from the British Patent Nos. 1,249,490, and 1,327,481, and British patent applications Nos. 19959/72, 32909/72, 51384/72, 53043/72, 3658/73 and 42050/73) or can be prepared by conventional methods for preparing analogous known compounds.

The step of converting a compound of formula IV to a compound of formula III is carried out by a reduction process, e.g. by using lithium aluminium hydride, but other agents and processes can be used as well. The benzyl alcohol derivative of formula III is thereafter converted into a compound of formula II by conventional methods for the preparation of esters of mineralic and sulphonic acids with alcohols, well known to the man skilled in the art.

In another method, a compound of the formula V

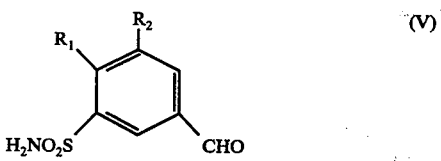

(V)

in which $R_1$ and $R_2$ have the above meanings, is converted into a compound of formula I by a reductive alkylation, e.g. by reaction with an amine $H_2NR_3$, in which $R_3$ has the above meanings, followed by a hydrogenation in the presence of a suitable catalyst, or by reduction, e.g. with alkali metal borohydrides. The hydrogenation can also be carried out simultaneously with the reaction with the amine $H_2NR_3$.

The starting material of formula V can for instance be prepared by oxidizing a compound of formula III, for instance with chromic anhydride in pyridine, or with another suitable oxidating agent. The compounds of of formula V can also be prepared from a compound of formula IV or another suitable acid derivative, e.g. an acid halide or anhydride corresponding to formula IV by subjecting such compounds to a reduction under milder conditions than those described above in connection with the first method.

In still another method, a compound of the formula

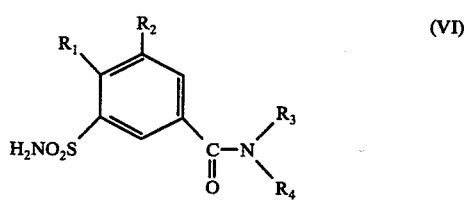

(VI)

in which $R_1$, $R_2$, $R_3$, and $R_4$ have the above meanings, is subjected to a reduction process, for instance with lithium aluminium hydride, to form the desired compound of formula I.

The compounds of formula VI can be prepared from the free acids corresponding to the compounds of formula IV, the free acids being converted into a reactive derivative thereof, such as an acid halide, or an anhydride, the reactive derivative thus obtained being reacted with an amine $HNR_3R_4$, $R_3$ and $R_4$ having the above meanings.

In a further method, a compound of the formula VII

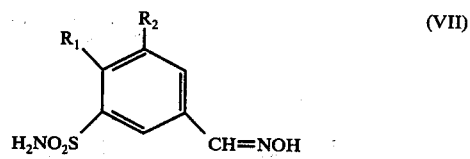

(VII)

in which $R_1$ and $R_2$ have the above meanings, is subjected to a reduction process, forming a compound of formula I, in which $R_3$ and $R_4$ stand for hydrogen.

The compounds of formula VII can be prepared from the compounds of formula V by reaction with hydroxylamine.

Still a further method for producing a compound of formula I, in which $R_3$ and $R_4$ stand for hydrogen, consists in subjecting a compound of formula VIII

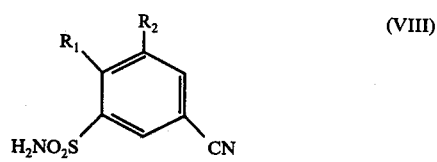

(VIII)

in which $R_1$ and $R_2$ have the meanings defined above, to a reduction process.

The starting material of formula VIII can be prepared from compounds of formula VI ($R_3=R_4=H$) by dehydration.

Compounds of formula I can further be prepared by other methods, e.g. as illustrated by one of the following reaction schemes:

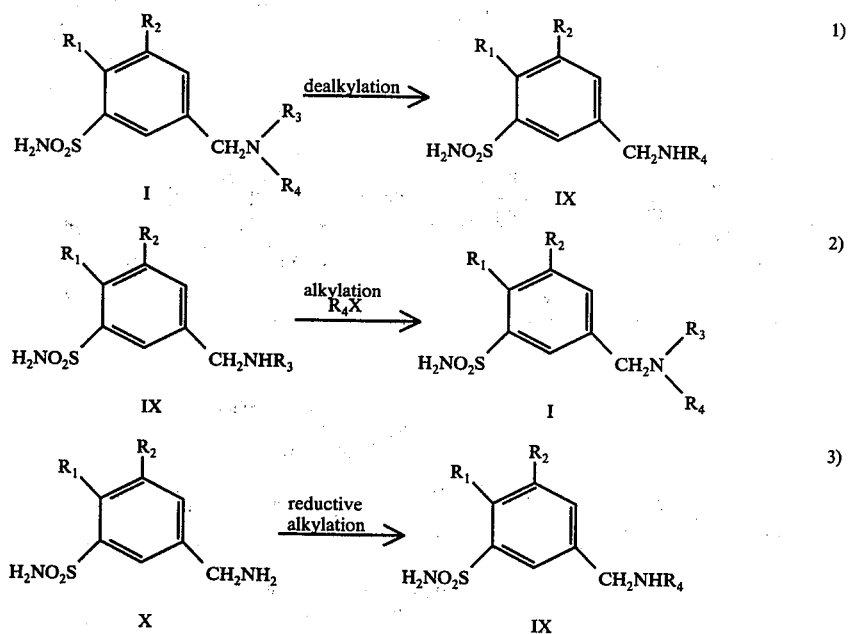

4)
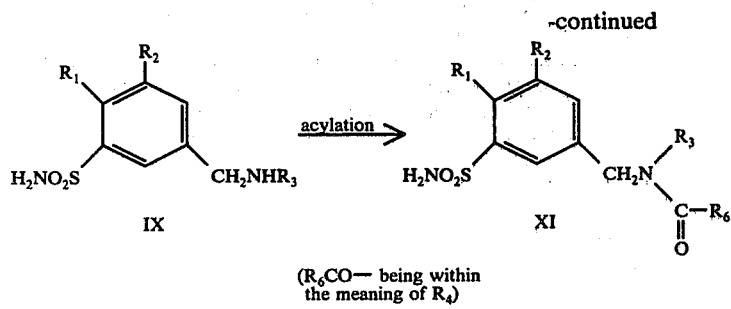
($R_6CO-$ being within the meaning of $R_4$)
5)
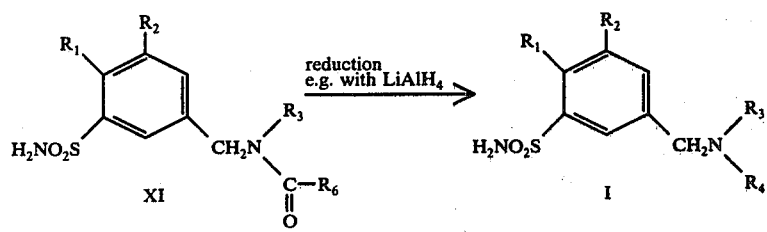
6)
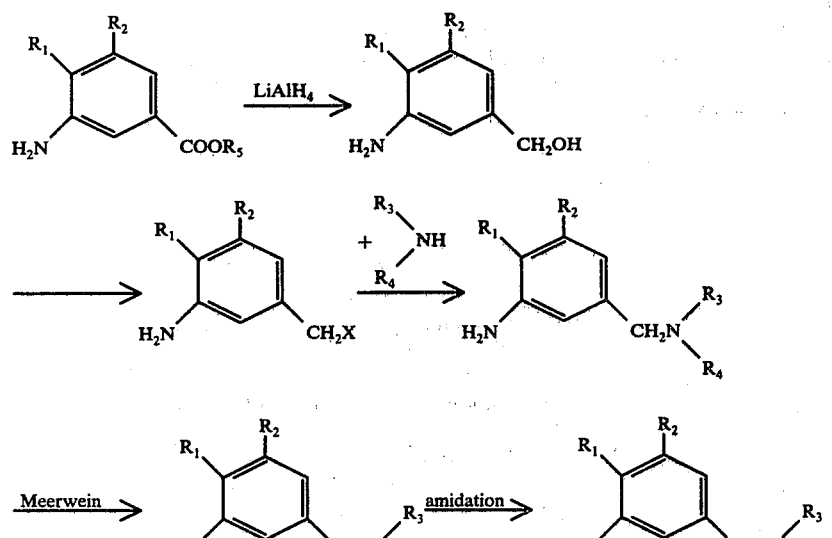
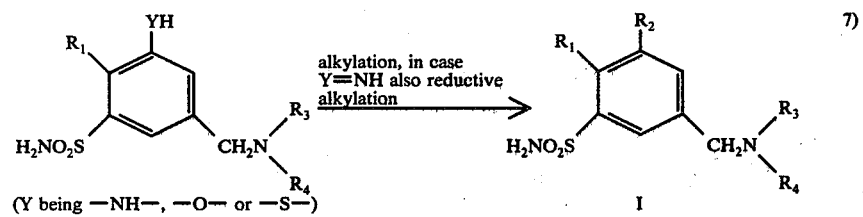
(Hal standing for halogen)
7)
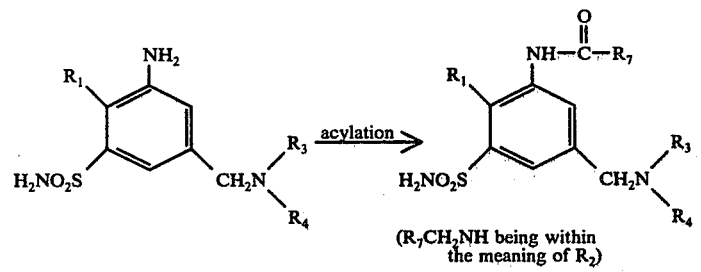
(Y being $-NH-$, $-O-$ or $-S-$)
8)
($R_7CH_2NH$ being within the meaning of $R_2$)

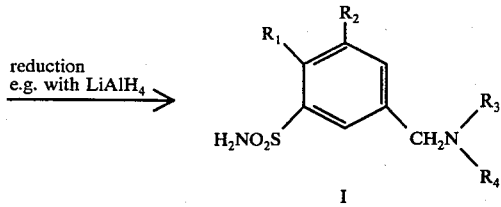

The intermediates of formulae III, V and VII are new compounds, which can also be used for the production of other final compounds than the ones covered by formula I. Therefore the compounds of formulae III, V and VII also form part of the present invention.

It should be mentioned, too, that the compounds of formula III and V show a pronounced diuretic and saluretic activity. The compounds of formula VII are especially valuable in causing an increased urinary excretion of water and sodium chloride while the excretion of potassium is not influenced.

Another object of the invention resides in the selection of a dose of the compounds of the invention which dose can be administered so that the desired activity is achieved without simultaneous secondary effects. In the human therapy, the compounds and their salts are conveniently administered (to adults) in dosage units containing not less than 0.1 mg and up to 50 mg, preferably from 0.25 to 25 mg, calculated as the compound of formula I.

By the term "dosage unit" is meant a unitary, i.e., a single dose which is capable of being administered to a patient, and which may be readily handled and packed, remaining as a physically stable unit dose comprising either the active material as such or a mixture of it with solid or liquid pharmaceutical diluents or carriers.

In the form of a dosage unit, the compound may be administered once or more times a day at appropriate intervals, always depending, however, on the condition of the patient, and in accordance with the prescription made by the medical practitioner.

Thus an appropriate daily dose would be an amount of from 0.25 to 100 mg of a compound of formula I.

If the composition is to be injected, a sealed ampoule, a vial or a similar container may be provided containing a parenterally acceptable aqueous or oily injectable solution or dispersion of the active material as the dosage unit.

The parenteral preparations are in particular useful in the treatment of conditions in which a quick response to the treatment is desirable. In the continuous therapy the tablets or capsules may be the appropriate form of pharmaceutical preparation, e.g. owing to the prolonged effect obtained when the drug is given orally. If desired, the compounds may be administered in the form of sustained-release formulations.

In the treatment of various diseases, such tablets may advantageously contain other active agents as mentioned hereinbefore.

Still another object of the invention is to provide a method of treating patients suffering from oedematous conditions, e.g. cardiac, hepatic, renal, and pulmonary oedema, and from pathological conditions which cause an abnormal retention of the electrolytes in the body, and/or from hypertension, the method comprising administering to adult patients from 0.25 to 100 mg per day of a compound of formula I or an equivalent amount of a salt as defined above, optionally together with other active agents as described above.

It is to be understood that it is not necessary to administrate both the active components of the formula I and other therapeutic agents, as described above by using a composition according to the invention which contains both these components. The most important thing is that both the active components are administered in such a way that they are able to act synergistically within the body. As a rule this means that both components must be administered simultaneously, i.e., at such an interval that it is possible for the compounds to act synergistically.

Preferably, the compound is given in the form of the dosage units aforesaid.

The invention will be further described in the following Examples which are not to be construed as limiting the invention.

EXAMPLE 1

4-Benzyl-3-methylthio-5-sulfamylbenzyl alcohol

To a stirred mixture of lithium aluminium hydride (24 g) and dry diethyl ether (500 ml), a solution of ethyl 4-benzyl-3-methylthio-5-sulfamylbenzoate (85 g) in dry diethyl ether (3 liters) is dropwise added during 1–1.5 hours. After additional stirring for 3 hours the mixture is cooled, and ethyl acetate (60 ml) followed by water (100 ml) and 4 N hydrochloric acid (1 liter) are very cautiously added dropwise. The organic layer is separated, washed with 4 N hydrochloric acid and with water, and dried in the presence of magnesium sulphate. After filtration, the solvents are removed in vacuo to yield crude 4-benzyl-3-methylthio-5-sulfamylbenzylalcohol. After recrystallization from ethanol it is obtained with a melting point of 190°–192° C.

EXAMPLE 2

3-Amino-4-phenoxy-5-sulfamylbenzyl alcohol

To a stirred mixture of lithium aluminium hydride (12.5 g) and dry dioxane (250 ml), a solution of ethyl 3-amino-4-phenoxy-5-sulfamylbenzoate (50 g) in dry dioxane (250 ml) is dropwise added at 90° C during about one hour. After additonal stirring and heating for 3 hours the mixture is cooled, and ethyl acetate (25 ml) followed by water (50 ml) and 4 N acetic acid (310 ml) are very cautiously added dropwise. The solvents are thereafter removed in vacuo, and the residue is extracted with ethyl acetate (1 liter). The insoluble inorganic material is removed by filtration, and the filtrate is washed with aqueous sodium hydrogen carbonate and with water, and is then dried in the presence of magnesium sulphate. After filtration, the solvent is removed in vacuo to yield crude 3-amino-4-phenoxy-5-sulfamylbenzyl alcohol. After recrystallization from aqueous ethanol it is obtained with a melting point of 170° C.

EXAMPLE 3

3-Amino-4-(3'-trifluoromethylphenoxy)-5-sulfamylbenzyl alcohol

To a stirred mixture of lithium aluminium hydride (5.0 g) and dry 1,2-dimethoxyethane (100 ml), a solution of ethyl 3-amino-4-(3'-trifluoromethylphenoxy)-5-sulfamylbenzoate (20 g) in dry 1,2-dimethoxyethane (100 ml) is dropwise added at 100° C during about 1 hour. After additional stirring and heating for 3 hours, the mixture is cooled, and ethyl acetate (10 ml) followed by water (20 ml) and 4 N acetic acid (125 ml) are very cautiously added dropwise. The solvents are thereafter removed in vacuo and the residue is extracted with ethyl acetate (300 ml). The insoluble inorganic material is removed by filtration, and the filtrate is washed with aqueous sodium hydrogen carbonate and with water, and is then dried in the presence of magnesium sulphate. After filtration, the solvent is removed in vacuo to yield crude 3-amino-4-(3'trifluoromethylphenoxy)-5-sulfamylbenzyl alcohol. After recrystallization from diethyl ether/petroleum ether it is obtained with a melting point of 133°–134° C.

EXAMPLE 4

3-Amino-4-benzyl-5-sulfamylbenzyl alcohol

To a stirred mixture of lithium aluminium hydride (12 g) and dry diethyl ether (350 ml), a solution of methyl 3-amino-4-benzyl-5-sulfamylbenzoate (30 g) in dry pyridine (300 ml) is dropwise added during 1–1.5 hours. After additional stirring for 3 hours, the mixture is cooled and ethyl acetate (25 ml) followed by water (50 ml) are very cautiously added dropwise. After stirring for a further 30 minutes, the solids are collected by filtration and dried in air. The filter cake is treated with hot 4 N hydrochloric acid (about 500 ml) to dissolve inorganic material. After cooling 3-amino-4-benzyl-5-sulfamylbenzyl alcohol is collected by filtration and dried in air. After recrystallization from aqueous ethanol it is obtained with a melting point of 159°–161° C.

EXAMPLE 5

3-Methylamino-4-phenoxy-5-sulfamylbenzyl alcohol

A mixture of 3-amino-4-phenoxy-5-sulfamylbenzyl alcohol (8.8 g; prepared as described in Example 2), methyl iodide (2.1 ml), sodium hydrogen carbonate (5.0 g) and hexamethylphosphoric triamide (45 ml) is stirred at 22°–25° C for 18 hours. The mixture is then diluted with water (about 500 ml) to precipitate crude 3-methylamino-4-phenoxy-5-sulfamylbenzyl alcohol. After recrystallization from aqueous ethanol it is obtained with a melting point of 167°–168° C.

EXAMPLE 6

3-(2'-Furfurylamino)-4-phenoxy-5-sulfamylbenzyl alcohol

A solution of 3-amino-4-phenoxy-5-sulfamylbenzyl alcohol (14.7 g; prepared as described in Example 2) and furfural (6 ml) in methanol (150 ml) is refluxed for 18 hours. Sodium borohydride (40 g) is thereafter during about one hour added in portions to the stirred solution, keeping the temperature at 0°–5° C. by external cooling. After additional stirring for 2 hours, 2 N acetic acid (100 ml) is cautiously added dropwise, whereafter the methanol is removed in vacuo. The residue is diluted with water to precipitate crude 3-(2'-furfurylamino)-4-phenoxy-5-sulfamylbenzyl alcohol. After recrystallization from ethanol it is obtained with a melting point of 162°–163° C.

EXAMPLES 7 – 50

By following, as defined in Table I below, the procedures described in Examples 1–6, but using as starting materials an equimolar amount of the appropriate alkyl 4-$R_1$-3-$R_2$-5-sulfamylbenzoate or the appropriate 4-$R_1$-3-$NH_2$-5-sulfamylbenzyl alcohol, and, when following the procedures of Examples 5 or 6, the appropriate alkyl halogenide or aldehyde, respectively, the 4-$R_1$-3-$R_2$-5-sulfamylbenzyl alcohols of Table I are obtained.

Table I.

| Ex. No. | Example(s) in which the procedure(s) used is (are) described | Reaction product | Mp ° C. |
|---|---|---|---|
| 7 | 5 | 3-ethylamino-4-phenoxy-5-sulfamylbenzyl alcohol | 165–167 |
| 8 | 5 | 3-allylamino-4-phenoxy-5-sulfamylbenzyl alcohol | 141–142 |
| 9 | 4 and 5 | 4-phenoxy-3-propargylamino-5-sulfamylbenzyl alcohol | 164–166 |
| 10 | 4 and 5 | 3-n-butylamino-4-phenoxy-5-sulfamylbenzyl alcohol | 157–158 |
| 11 | 5 | 3-crotylamino-4-phenoxy-5-sulfamylbenzyl alcohol | 171–173 |
| 12 | 5 | 3-n-pentylamino-4-phenoxy-5-sulfamylbenzyl alcohol | 142–144 |
| 13 | 5 | 3-isopentylamino-4-phenoxy-5-sulfamylbenzyl alcohol | 121–123 |
| 14 | 4 and 5 | 3-benzylamino-4-phenoxy-5-sulfamylbenzyl alcohol | 205–206 |
| 15 | 6 | 4-phenoxy-3-(2'-thenylamino)-5-sulfamylbenzyl alcohol | 194–196 |
| 16 | 6 | 4-phenoxy-3-(2'-pyridylmethylamino)-5-sulfamylbenzyl alcohol | 169–170 |
| 17 | 6 | 4-phenoxy-3-(3'-pyridylmethylamino)-5-sulfamylbenzyl alcohol | 198–200 |
| 18 | 2 | 3-amino-4-(4'-methoxyphenoxy)-5-sulfamylbenzyl alcohol | 172–173 |
| 19 | 5 | 3-n-butylamino-4-(4'-methoxyphenoxy)-5-sulfamylbenzyl alcohol | 129–131 |
| 20 | 5 | 3-benzylamino-4-(4'-methoxyphenoxy)-5-sulfamylbenzyl alcohol | 200–202 |
| 21 | 5 | 3-benzylamino-4-(3'-trifluoromethylphenoxy)-5-sulfamylbenzyl alcohol | 153–155 |
| 22 | 2 | 3-amino-4-phenylthio-5-sulfamylbenzyl alcohol | 168 |

Table I.-continued

| Ex. No. | Example(s) in which the procedure(s) used is (are) described | Reaction product | Mp ° C. |
|---|---|---|---|
| 23 | 5 | 3-n-butylamino-4-phenylthio-5-sulfamylbenzyl alcohol | 103–105 |
| 24 | 5 | 3-benzylamino-4-phenylthio-5-sulfamylbenzyl alcohol | 172–174 |
| 25 | 2 | 3-amino-4-(2'-methylphenylthio)-5-sulfamylbenzyl alcohol | 170–171 |
| 26 | 5 | 3-n-butylamino-4-(2'-methylphenylthio)-5-sulfamylbenzyl alcohol | 86–88 |
| 27 | 5 | 3-benzylamino-4-(2'-methylphenylthio)-5-sulfamylbenzyl alcohol | 170–172 |
| 28 | 2 | 3-amino-4-anilino-5-sulfamylbenzyl alcohol | 144–145 |
| 29 | 5 | 4-benzyl-3-ethoxy-5-sulfamylbenzyl alcohol | 144–145 |
| 30 | 5 | 4-anilino-3-benzylamino-5-sulfamylbenzyl alcohol | 135–137 |
| 31 | 2 | 3-amino-4-(4'-chloroanilino)-5-sulfamylbenzyl alcohol | 137–139 |
| 32 | 5 | 3-n-butylamino-4-(4'-chloroanilino)-5-sulfamylbenzyl alcohol | 129–131 |
| 33 | 5 | 3-benzylamino-4-(4'-chloroanilino)-5-sulfamylbenzyl alcohol | 145–147 |
| 34 | 1 and 5 | 4-benzyl-3-ethylamino-5-sulfamylbenzyl alcohol | 163–165 |
| 35 | 4 and 5 | 4-benzyl-3-n-butylamino-5-sulfamylbenzyl alcohol | 145–147 |
| 36 | 4 and 5 | 4-benzyl-3-benzylamino-5-sulfamylbenzyl alcohol | 179–180 |
| 37 | 6 | 4-benzyl-3-(2'-furfurylamino)-5-sulfamylbenzyl alcohol | 166–168 |
| 38 | 4 | 4-benzyl-3-methoxy-5-sulfamylbenzyl alcohol | 186–188 |
| 39 | 4 | 4-benzyl-3-ethoxy-5-sulfamuyl-benzyl alcohol | 115–117 |
| 40 | 4 | 4-benzyl-3-n-propoxy-5-sulfamylbenzyl alcohol | 118–119 |
| 41 | 1 | 4-benzyl-3-isopropoxy-5-sulfamylbenzyl alcohol | 152–153 |
| 42 | 4 | 4-benzyl-3-n-butoxy-5-sulfamylbenzyl alcohol | 111–115 |
| 43 | 4 | 4-benzyl-3-isopentyloxy-5-sulfamylbenzyl alcohol | 92–95 |
| 44 | 4 | 4-benzyl-3-benzyloxy-5-sulfamylbenzyl alcohol | 142–144 |
| 45 | 1 | 4-benzyl-3-ethylthio-5-sulfamylbenzyl alcohol | 117–118 |
| 46 | 1 | 3-allylthio-4-benzyl-5-sulfamylbenzyl alcohol | 93–94 |
| 47 | 1 | 4-benzyl-3-n-butylthio-5-sulfamylbenzyl alcohol | 109–111 |
| 48 | 1 | 4-benzyl-3-benzylthio-5-sulfamylbenzyl alcohol | 113–114 |
| 49 | 1 | 4-benzyl-3-(2'-phenethylthio)-5-sulfamylbenzyl alcohol | 124–125 |
| 50 | 2 | 4-benzyl-3-(2'-pyridylmethylthio)-5-sulfamylbenzyl alcohol | 129–131 |

EXAMPLE 51

4-Phenoxy-3-(4'-pyridylethyl-(2)-amino)-5-sulfamylbenzyl alcohol

A solution of 3-amino-4-phenoxy-5-sulfamylbenzyl alcohol (14.7 g; prepared as described in Example 2), 4-vinylpyridine (10 ml) and acetic acid (10 ml) in 2-methoxyethanol (75 ml) is heated on a steam-bath for 24 hours. The solution is then diluted with water (75 ml) to precipitate crude 4-phenoxy-3-(4'-pyridylethyl-(2)-amino)-5-sulfamylbenzyl alcohol. After recrystallization from ethanol it is obtained with a melting point of 188°–189° C.

EXAMPLE 52

3-Benzylamino-4-phenylsulfinyl-5-sulfamylbenzyl alcohol

A mixture of 3-benzylamino-4-phenylthio-5-sulfamylbenzyl alcohol (8.0 g; prepared as described in Example 24), hydrogenperoxide (10 ml, 30% in water) and acetic acid (80 ml) is stirred at 22°–25° C. for 24 hours. The resulting solution is diluted with water (40 ml) and cooled to precipitate crude 3-benzylamino-4-phenylsulfinyl-5-sulfamylbenzyl alcohol. After recrystallization from a mixture of ethanol and 2-methoxyethanol it is obtained with a melting point of 213°–214° C.

EXAMPLE 53

4-Benzyl-3-methylthio-5-sulfamylbenzyl bromide

4-Benzyl-3-methylthio-5-sulfamylbenzyl alcohol (10 g; prepared as described in Example 1) is while stirring added in portions to acetic acid saturated with dry hydrogen bromide (50 ml), and the mixture is stirred for 24 hours. The resulting solution is diluted with water (100 ml) and cooled to precipitate crude 4-benzyl-3-methylthio-5-sulfamylbenzyl bromide. After recrystallization from methanol it is obtained with a melting point of 149°–150° C.

EXAMPLES 54 – 60

By following the procedure described in Example 53 but replacing 4-benzyl-3-methylthio-5-sulfamylbenzyl alcohol with other 4-$R_1$-3-$R_2$-5-sulfamylbenzyl alcohols as defined in Table II below, the corresponding 4-$R_1$-3-

$R_2$-5-sulfamylbenzyl bromides of Table II are obtained.

Table II.

| Ex. No. | Example in which the starting material is described | Reaction product | Mp ° C. |
|---|---|---|---|
| 54 | 42 | 4-benzyl-3-n-butoxy-5-sulfamyl-benzyl bromide | 129–130 |
| 55 | 45 | 4-benzyl-3-ethylthio-5-sulfamyl-benzyl bromide | 129–131 |
| 56 | 46 | 3-allylthio-4-benzyl-5-sulfamyl-benzyl bromide | see below |
| 57 | 47 | 4-benzyl-3-n-butylthio-5-sulfamylbenzyl bromide | see below |
| 58 | 48 | 4-benzyl-3-benzylthio-5-sulfamylbenzyl bromide | see below |
| 59 | 49 | 4-benzyl-3-(2'-phenethylthio)-5-sulfamylbenzyl bromide | see below |
| 60 | 50 | 4-benzyl-3-(2'-pyridylmethyl-thio)-5-sulfamylbenzyl bromide | see below |

The benzylbromides of Examples 56–60 are obtained as oils or hygroscopic amorphous materials which are used as such in the next step without purification.

EXAMPLE 61

3-Amino-4-benzyl-5-sulfamylbenzyl bromide hydrobromide

3-Amino-4-benzyl-5-sulfamylbenzyl alcohol (12.5 g; prepared as described in Example 4) is while stirring added in portions to acetic acid saturated with dry hydrogen bromide (60 ml), and the mixture is stirred for 24 hours. The resulting solution is diluted with diethyl ether (150 ml) and cooled to precipitate 3-amino-4-benzyl-5-sulfamylbenzyl bromide hydrobromide as a hygroscopic material with a melting point of 195°–198° C.

EXAMPLES 62 – 88

By following the procedure described in Example 61 but replacing 3-amino-4-benzyl-5-sulfamylbenzyl alcohol with other 4-$R_1$-3-$R_2$-5-sulfamylbenzyl alcohols as defined in Table III below, the corresponding 4-$R_1$-3-$R_2$-5-sulfamylbenzyl bromide hydrobromides of Table III are obtained.

Table III

| Ex. No. | Ex. in which the starting material is described | Reaction product | Mp ° C. |
|---|---|---|---|
| 62 | 2 | 3-amino-4-phenoxy-5-sulfamylbenzyl bromide hydrobromide | 202–206 |
| 63 | 5 | 3-methylamino-4-phenoxy-5-sulfamyl-benzyl bromide hydrobromide | 185–187 |
| 64 | 7 | 3-ethylamino-4-phenoxy-5-sulfamyl-benzyl bromide hydrobromide | 136–138 |
| 65 | 8 | 3-allylamino-4-phenoxy-5-sulfamyl-benzyl bromide hydrobromide | 146–149 |
| 66 | 9 | 4-phenoxy-3-propargylamino-5-sulfamyl-benzyl bromide hydrobromide | 146–148 |
| 67 | 10 | 3-n-butylamino-4-phenoxy-5-sulfamyl-benzyl bromide hydrobromide | 178–181 |
| 68 | 12 | 3-n-pentylamino-4-phenoxy-5-sulfamyl-benzyl bromide hydrobromide | 177–180 |
| 69 | 13 | 3-isopentylamino-4-phenoxy-5-sulfamyl-benzyl bromide hydrobromide | see below |
| 70 | 14 | 3-benzyl-4-phenoxy-5-sulfamyl-benzyl bromide hydrobromide | 146–147 |
| 71 | 16 | 4-phenoxy-3-(2'-pyridylmethylamino)-5-sulfamylbenzyl bromide dihydrobromide | see below |
| 72 | 17 | 4-phenoxy-3-(3'-pyridylmethylamino)-5-sulfamylbenzyl bromide dihydrobromide | see below |
| 73 | 19 | 3-n-butylamino-4-(4'-methoxyphenoxy)-5-sulfamylbenzyl bromide hydrobromide | 178–180 |
| 74 | 20 | 3-benzylamino-4-(4'-methoxyphenoxy)-5-sulfamylbenzyl bromide hydrobromide | 220–225 |
| 75 | 21 | 3-benzylamino-4-(3'-trifluoromethyl-phenoxy)-5-sulfamylbenzyl bromide hydrobromide | see below |
| 76 | 23 | 3-n-butylamino-4-phenylthio-5-sulfamyl-benzyl bromide hydrobromide | see below |
| 77 | 24 | 3-benzylamino-4-phenylthio-5-sulfamyl-benzyl bromide hydrobromide | 139–141 |
| 78 | 26 | 3-n-butylamino-4-(2'-methylphenylthio)-5-sulfamylbenzyl bromide hydrobromide | see below |
| 79 | 27 | 3-benzylamino-4-(2'-methylphenylthio)-5-sulfamylbenzyl bromide hydrobromide | 144–145 |
| 80 | 29 | 4-anilino-3-n-butylamino-5-sulfamyl-benzyl bromide hydrobromide | 195–200 |
| 81 | 30 | 4-anilino-3-benzylamino-5-sulfamyl-benzyl bromide hydrobromide | 108–111 |
| 82 | 32 | 3-n-butylamino-4-(4'-chloroanilino)-5-sulfamylbenzyl bromide hydrobromide | 215–218 |
| 83 | 33 | 3-benzylamino-4-(4'-chloroanilino)-5-sulfamylbenzyl bromide hydrobromide | see below |
| 84 | 34 | 4-benzyl-3-ethylamino-5-sulfamyl-benzyl bromide hydrobromide | see below |
| 85 | 35 | 4-benzyl-3-n-butylamino-5-sulfamyl-benzyl bromide hydrobromide | 213–215 |
| 86 | 36 | 4-benzyl-3-benzylamino-5-sulfamyl-benzyl bromide hydrobromide | 176–177 |
| 87 | 51 | 4-phenoxy-3-(4'-pyridylethyl-(2)-amino)-5-sulfamylbenzyl bromide dihydrobromide | 203–205 |
| 88 | 52 | 3-benzylamino-4-phenylsulfinyl-5-sulfamylbenzyl bromide hydrobromide | see below |

The benzylbromide hydrobromides of Examples 69, 71, 72, 75, 76, 78, 83, 84 and 88 are obtained as hygroscopic solids or semisolids, which are used as such in the next step without purification.

EXAMPLE 89

3-Methylamino-4-phenoxy-5-sulfamylbenzaldehyde

To a stirred mixture of dry pyridine (15 ml) and dry methylene chloride (225 ml), chromic anhydride (9.0 g) is added in one portion, and the mixture is stirred for 15 minutes. A solution of 3-methylamino-4-phenoxy-5-sulfamylbenzyl alcohol (4.6g; prepared as described in Example 5) in acetone (25 ml) is then added in one portion and the mixture is stired for a further 15 minutes. The resulting inorganic precipitate is removed by filtration and the filtrate is evaporated in vacuo. The residue is extracted with diethyl ether (300 ml) and filtered to remove a small amount of insoluble material. The diethyl ether is removed in vacuo to yield crude 3-methylamino-4-phenoxy-5-sulfamylbenzaldehyde. After recrystallization from ethanol it is obtained with a melting point of 166°-167° C.

EXAMPLES 90-109

By following the procedure described in Example 89 but replacing 3-methylamino-4-phenoxy-5-sulfamylbenzyl alcohol with equimolor amounts of other 4-$R_1$-3-$R_2$-5-sulfamylbenzyl alcohols as defined in Table IV below, the corresponding 4-$R_1$-3-$R_2$-5-sulfamylbenzaldehydes of Table IV are obtained.

Table IV

| Ex. No. | Ex. in which the starting material is described | Reaction product | Mp ° C. |
|---|---|---|---|
| 90 | 7 | 3-ethylamino-4-phenoxy-5-sulfamyl-benzaldehyde | 165–166 |
| 91 | 8 | 3-allylamino-4-phenoxy-5-sulfamyl-benzaldehyde | 109–111 |
| 92 | 9 | 4-phenoxy-3-propargylamino-5-sulfamylbenzaldehyde | 105–108 |
| 93 | 10 | 3-n-butylamino-4-phenoxy-5-sulfamyl-benzaldehyde | 152–153 |
| 94 | 11 | 3-crotylamino-4-phenoxy-5-sulfamyl-benzaldehyde | 176–178 |
| 95 | 12 | 3-n-pentylamino-4-phenoxy-5-sulfamyl-benzaldehyde | 147–149 |
| 96 | 6 | 3-(2'-furfurylamino)-4-phenoxy-5-sulfamylbenzaldehyde | 154–156 |
| 97 | 15 | 4-phenoxy-5-sulfamyl-3-(2'-thenyl-amino)benzaldehyde | 164–166 |
| 98 | 51 | 4-phenoxy-3-(4'-pyridylethyl-(2)-amino)-5-sulfamylbenzaldehyde | 175–177 |
| 99 | 19 | 3-n-butylamino-4-(4'-methoxyphenoxy)-5-sulfamylbenzaldehyde | 133–135 |
| 100 | 20 | 3-benzylamino-4-(4'-methoxyphenoxy)-5-sulfamylbenzaldehyde | 191–193 |
| 101 | 35 | 4-benzyl-3-n-butylamino-5-sulfamyl-benzaldehyde | 127–129 |
| 102 | 37 | 4-benzyl-3-(2'-furfurylamino)-5-sulfamylbenzaldehyde | 147–149 |
| 103 | 38 | 4-benzyl-3-methoxy-5-sulfamyl-benzaldehyde | 139–141 |
| 104 | 39 | 4-benzyl-3-ethoxy-5-sulfamyl-benzaldehyde | 137–138 |
| 105 | 40 | 4-benzyl-3-n-propoxy-5-sulfamyl-benzaldehyde | 133–134 |
| 106 | 41 | 4-benzyl-3-isopropoxy-5-sulfamyl-benzaldehyde | 128–130 |
| 107 | 42 | 4-benzyl-3-n-butoxy-5-sulfamyl-benzaldehyde | 136–137 |
| 108 | 43 | 4-benzyl-3-isopentyloxy-5-sulfamyl-benzaldehyde | 115–117 |
| 109 | 44 | 4-benzyl-3-benzyloxy-5-sulfamyl-benzaldehyde | 173–174 |

EXAMPLE 110

(3-Amino-4-benzyl-5-sulfamylbenzyl)-n-butylamine

A mixture of 3-amino-4-benzyl-5-sulfamylbenzyl bromide hydrobromide (1.1 g; prepared as described in Example 61), n-butylamine (5.0 ml) and methanol (10 ml) is stirred at 22°–25° C. for 24 hours. The resulting solution is then diluted with water (20 ml) to precipitate crude (3-amino-4-benzyl-5-sulfamylbenzyl)-n-butylamine. After filtration and recrystallization from aqueous ethanol it is obtained with a melting point of 141°–143° C.

EXAMPLES 111-190

By following the procedure described in Example 110 but using as starting materials the appropriate 4-$R_1$-3-$R_2$-5-sulfamylbenzyl bromide (or its hydrobromide) and amine as defined in Table V below, the corresponding 4-$R_1$-3-$R_2$-5-sulfamyl N-substituted benzylamines of Table V are obtained.

Table V

| Ex. No. | Example in which the benzyl-bromide used is described | Amine used in the reaction | Reaction product | Mp ° C. | |
|---|---|---|---|---|---|
| 111 | 62 | allylamine | (3-amino-4-phenoxy-5-sulfamyl-benzyl)allylamine hydrate | 95 | 98 |
| 112 | 63 | isopentylamine | (3-methylamino-4-phenoxy-5-sulfamylbenzyl)isopentylamine | | |

Table V-continued

| Ex. No. | Example in which the benzyl-bromide used is described | Amine used in the reaction | Reaction product | Mp ° C. |
|---|---|---|---|---|
| 113 | 65 | isopropylamine | (3-allylamino-4-phenoxy-5-sulfamylbenzyl)isopropylamine hydrate | 86–88 |
| 114 | 66 | isopropylamine | (4-phenoxy-3-propargylamino-5-sulfamylbenzyl)isopropylamine | 97–100 |
| 115 | 67 | methylamine | (3-n-butylamino-4-phenoxy-5-sulfamylbenzyl)methylamine | 155–157 |
| 116 | 67 | ethylamine | (3-n-butylamino-4-phenoxy-5-sulfamylbenzyl)ethylamine | 156–158 |
| 117 | 67 | n-propylamine | (3-n-butylamino-4-phenoxy-5-sulfamylbenzyl)-n-propylamine | 152–153 |
| 118 | 67 | isopropylamine | (3-n-butylamino-4-phenoxy-5-sulfamylbenzyl)isopropylamine | 127–129 |
| 119 | 67 | n-butylamine | (3-n-butylamino-4-phenoxy-5-sulfamylbenzyl)-n-butylamine | 131–133 |
| 120 | 67 | isobutylamine | (3-n-butylamino-4-phenoxy-5-sulfamylbenzyl)isobutylamine | 108–110 |
| 121 | 67 | sec-butylamine | (3-n-butylamino-4-phenoxy-5-sulfamylbenzyl)sec-butylamine | 126–127 |
| 122 | 67 | tert-butylamine | (3-n-butylamino-4-phenoxy-5-sulfamylbenzyl)tert-butyl-amine hydrate | 162–163 |
| 123 | 67 | n-hexylamine | (3-n-butylamino-4-phenoxy-5-sulfamylbenzyl)-n-hexylamine | 109–111 |
| 124 | 67 | allylamine | (3-n-butylamino-4-phenoxy-5-sulfamylbenzyl)allylamine | 74–76 |
| 125 | 67 | 2-methylallyl-amine | (3-n-butylamino-4-phenoxy-5-sulfamylbenzyl)-2-methyl-allylamine | 111–113 |
| 126 | 67 | dimethylamine (40% in water) | (3-n-butylamino-4-phenoxy-5-sulfamylbenzyl)dimethylamine | 63–64 |
| 127 | 67 | diethylamine | (3-n-butylamino-4-phenoxy-5-sulfamylbenzyl)diethylamine | 97–98 |
| 128 | 67 | n-butylmethyl-amine | (3-n-butylamino-4-phenoxy-5-sulfamylbenzyl)-n-butylmethyl-amine | 116–117 |
| 129 | 67 | ethanolamine | (3-n-butylamino-4-phenoxy-5-sulfamylbenzyl)ethanolamine | 103–105 |
| 130 | 67 | N-methyl-ethanolamine | N-(3-n-butylamino-4-phenoxy-5-sulfamylbenzyl)-N-methyl-2-hydroxyethylamine | 182–183 |
| 131 | 67 | 3-aminopropanol | (3-n-butylamino-4-phenoxy-5-sulfamylbenzyl)-3-hydroxy-propylamine | 121–122 |
| 132 | 67 | 1-amino-2-propanol | (3-n-butylamino-4-phenoxy-5-sulfamylbenzyl)-2-hydroxy-propylamine | 163–164 |
| 133 | 67 | 2-amino-2-methyl-1-propanol | (3-n-butylamino-4-phenoxy-5-sulfamylbenzyl)-1,1-dimethyl-2-hydroxyethylamine | 169–170 |
| 134 | 67 | diethanolamine | (3-n-butylamino-4-phenoxy-5-sulfamylbenzyl)diethanolamine | 119–121 |
| 135 | 67 | 2-methoxyethyl-amine | (3-n-butylamino-4-phenoxy-5-sulfamylbenzyl)-2-methoxy-ethylamine | 60–62 |
| 136 | 67 | benzylamine | (3-n-butylamino-4-phenoxy-5-sulfamylbenzyl)benzylamine | 100–101 |
| 137 | 67 | aminodiphenyl-methane | (3-n-butylamino-4-phenoxy-5-sulfamylbenzyl)-α-phenyl-benzylamine | 86–87 |
| 138 | 67 | 4-methoxybenzyl-amine | (3-n-butylamino-4-phenoxy-5-sulfamylbenzyl)-4-methoxy-benzylamine hydrate | 134–136 |
| 139 | 67 | 2-phenethyl-amine | (3-n-butylamino-4-phenoxy-5-sulfamylbenzyl)-2-phenethyl-amine | 76–78 |
| 140 | 67 | homoveratryl-amine | (3-n-butylamino-4-phenoxy-5-sulfamylbenzyl)-3,4-dimethoxy-2-phenethylamine hydrate | 128–129 |
| 141 | 67 | 2-phenylthio-ethylamine | (3-n-butylamino-4-phenoxy-5-sulfamylbenzyl)-2-phenylthio-ethylamine | 76–80 |
| 142 | 67 | 2-furfurylamine | (3-n-butylamino-4-phenoxy-5-sulfamylbenzyl)-2-furfuryl-amine | 97–99 |
| 143 | 67 | 2-tetrahydro-furfurylamine | (3-n-butylamino-4-phenoxy-5-sulfamylbenzyl)-2-tetrahydro-furfurylamine | 104–105 |
| 144 | 67 | N-methyl-2-furfurylamine | N-(3-n-butylamino-4-phenoxy-5-sulfamylbenzyl)-N-methyl-2-furfurylamine | 114–116 |
| 145 | 67 | N-methyl-2-tetrahydro-furfurylamine | N-(3-n-butylamino-4-phenoxy-5-sulfamylbenzyl)-N-methyl-2-tetrahydrofurfurylamine | 79–81 |
| 146 | 67 | 2-picolylamine | (3-n-butylamino-4-phenoxy-5-sulfamylbenzyl)-2-picolylamine | 127–128 |
| 147 | 68 | isopropylamine | (3-n-pentylamino-4-phenoxy-5- | 112–114 |

Table V-continued

| Ex. No. | Example in which the benzyl-bromide used is described | Amine used in the reaction | Reaction product | Mp ° C. |
|---|---|---|---|---|
| 148 | 69 | n-pentylamine | sulfamylbenzyl)isopropylamine (3-isopentylamino-4-phenoxy-5-sulfamylbenzyl)-n-pentylamine hemihydrate | 116–117 |
| 149 | 70 | dimethylamine | (3-benzylamino-4-phenoxy-5-sulfamylbenzyl)dimethylamine | 100–103 |
| 150 | 70 | allylamine | (3-benzylamino-4-phenoxy-5-sulfamylbenzyl)allylamine | 156–158 |
| 151 | 70 | n-butylamine | (3-benzylamino-4-phenoxy-5-sulfamylbenzyl)-n-butylamine | 139–141 |
| 152 | 70 | benzylamine | (3-benzylamino-4-phenoxy-5-sulfamylbenzyl)benzylamine | 108–110 |
| 153 | 73 | isopropylamine | (3-n-butylamino-4-(4'-methoxyphenoxy)-5-sulfamylbenzyl)isopropylamine hydrate | 129–131 |
| 154 | 74 | allylamine | (3-benzylamino-4-(4'-methoxyphenoxy)-5-sulfamylbenzyl)allylamine | 91–94 |
| 155 | 74 | benzylamine | (3-benzylamino-4-(4'-methoxyphenoxy)-5-sulfamylbenzyl)benzylamine | 166–167 |
| 156 | 75 | dimethylamine | (3-benzylamino-4-(3'-trifluoromethylphenoxy)-5-sulfamylbenzyl)dimethylamine dihydrate | 181–183 |
| 157 | 76 | isopropylamine | (3-n-butylamino-4-phenylthio-5-sulfamylbenzyl)isopropylamine | 97–100 |
| 158 | 76 | allylamine | (3-n-butylamino-4-phenylthio-5-sulfamylbenzyl)allylamine | 130–131 |
| 159 | 77 | isopropylamine | (3-benzylamino-4-phenylthio-5-sulfamylbenzyl)isopropylamine hydrate | 124–126 |
| 160 | 77 | allylamine | (3-benzylamino-4-phenylthio-5-sulfamylbenzyl)allylamine | 57–59 |
| 161 | 77 | benzylamine | (3-benzylamino-4-phenylthio-5-sulfamylbenzyl)benzylamine | 118–119 |
| 162 | 79 | 3-picolylamine | (3-benzylamino-4-(2'-methylphenylthio)-5-sulfamylbenzyl)-3-picolylamine dihydrate | 100–102 |
| 163 | 80 | isopropylamine | (4-anilino-3-n-butylamino-5-sulfamylbenzyl)isopropylamine | 96–99 |
| 164 | 80 | allylamine | (4-anilino-3-n-butylamino-5-sulfamylbenzyl)allylamine | 123–125 |
| 165 | 81 | allylamine | (4-anilino-3-benzylamino-5-sulfamylbenzyl)allylamine | 163–165 |
| 166 | 81 | benzylamine | (4-anilino-3-benzylamino-5-sulfamylbenzyl)benzylamine | 192–194 |
| 167 | 83 | isopropylamine | (3-benzylamino-4-(4'-chloroanilino)-5-sulfamylbenzyl)isopropylamine | 153–156 |
| 168 | 83 | allylamine | (3-benzylamino-4-(4'-chloroanilino)-5-sulfamylbenzyl)allylamine | 190–191 |
| 169 | 83 | benzylamine | (3-benzylamino-4-(4'-chloroanilino)-5-sulfamylbenzyl)benzylamine | 163–164 |
| 170 | 61 | benzylamine | (3-amino-4-benzyl-5-sulfamylbenzyl)benzylamine, sesquihydrate | 153–155 61–63 |
| 171 | 84 | methylamine | (4-benzyl-3-ethylamino-5-sulfamylbenzyl)methylamine hemihydrate | 101–103 |
| 172 | 85 | dimethylamine | (4-benzyl-3-n-butylamino-5-sulfamylbenzyl)dimethylamine | 112–113 |
| 173 | 85 | allylamine | (4-benzyl-3-n-butylamino-5-sulfamylbenzyl)allylamine | 154–155 |
| 174 | 85 | n-butylamine | (4-benzyl-3-n-butylamino-5-sulfamylbenzyl)-n-butylamine | 139–141 |
| 175 | 85 | benzylamine | (4-benzyl-3-n-butylamino-5-sulfamylbenzyl)benzylamine hemihydrate | 103–105 |
| 176 | 86 | dimethylamine | (4-benzyl-3-benzylamino-5-sulfamylbenzyl)dimethylamine hydrate | 79–81 |
| 177 | 86 | allylamine | (4-benzyl-3-benzylamino-5-sulfamylbenzyl)allylamine | 141–143 |
| 178 | 86 | n-butylamine | (4-benzyl-3-benzylamino-5-sulfamylbenzyl)-n-butylamine | 139–140 |
| 179 | 86 | benzylamine | (4-benzyl-3-benzylamino-5-sulfamylbenzyl)benzylamine | 140–141 |
| 180 | 54 | dimethylamine | (4-benzyl-3-n-butoxy-5-sulfamylbenzyl)dimethylamine | 110–111 |
| 181 | 54 | allylamine | (4-benzyl-3-n-butoxy-5-sulfamylbenzyl)allylamine | 117–118 |
| 182 | 54 | isopropylamine | (4-benzyl-3-n-butoxy-5-sulfamylbenzyl)isopropylamine | 138–140 |
| 183 | 54 | n-butylamine | (4-benzyl-3-n-butoxy-4-sulfamylbenzyl)-n-butylamine | 120–123 |
| 184 | 54 | benzylamine | (4-benzyl-3-n-butoxy-5-sulfamyl- | |

Table V-continued

| Ex. No. | Example in which the benzyl-bromide used is described | Amine used in the reaction | Reaction product | Mp ° C. |
|---|---|---|---|---|
| 185 | 53 | dimethylamine | benzyl)benzylamine (4-benzyl-3-methylthio-5-sulfamylbenzyl)dimethylamine hydrate | 86– 87 / 88– 91 |
| 186 | 55 | 4-picolylamine | (4-benzyl-3-ethylthio-5-sulfamyl-benzyl)-4-picolylamine | 110–112 |
| 187 | 56 | n-hexylamine | (3-allylthio-4-benzyl-5-sulfamylbenzyl)-n-hexylamine hydrate | 90– 93 |
| 188 | 57 | isopropylamine | (4-benzyl-3-n-butylthio-5-sulfamylbenzyl)isopropylamine | 157–159 |
| 189 | 57 | allylamine | (4-benzyl-3-n-butylthio-5-sulfamylbenzyl)allylamine | 140–142 |
| 190 | 59 | n-butylamine | (4-benzyl-3-(2'-phenethylthio)-5-sulfamylbenzyl)-n-butylamine dihydrate | 96–100 |

EXAMPLE 191

(3-Ethylamino-4-phenoxy-5-sulfamylbenzyl)benzylamine hydrochloride

A mixture of 3-ethylamino-4-phenoxy-5-sulfamylbenzyl bromide hydrobromide (2.5 g; prepared as described in Example 64), benzylamine (10 ml) and methanol (20 ml) is stirred at 22°–25° C. for 24 hours. The resulting solution is then diluted with water (60 ml) to precipitate (3-ethylamino-4-phenoxy-5-sulfamylbenzyl)benzylamine as an oil. The oil is separated and dissolved in ethanol (20 ml), whereafter a saturated solution of dry hydrogen chloride in ethanol (2 ml) is added to precipitate the hydrochloride. After filtration and recrystallization from ethanol, (3-ethylamino-4-phenoxy-5-sulfamylbenzyl)benzylamine hydrochloride is obtained with a melting point of 220°–223° C.

EXAMPLES 192 – 215

By following the procedure described in Example 191 but using as starting materials the appropriate 4-$R_1$-3-$R_2$-5-sulfamylbenzyl bromide (or hydrobromide) and amine as defined in Table VI below, the corresponding 4-$R_1$-3-$R_2$-5-sulfamyl N-substituted benzylamine hydrochlorides of Table VI are obtained.

Table VI

| Ex. No. | Example in which the benzyl-bromide used is described | Amine used in the reaction | Reaction product | Mp ° C. |
|---|---|---|---|---|
| 192 | 67 | isopentylamine | (3-n-butylamino-4-phenoxy-5-sulfamylbenzyl)isopentylamine dihydrochloride | 211–213 |
| 193 | 67 | cyclohexyl-amine | (3-n-butylamino-4-phenoxy-5-sulfamylbenzyl)cyclohexylamine hydrochlorie | 238–239 |
| 194 | 67 | di-n-propyl-amine | (3-n-butylamino-4-phenoxy-5-sulfamylbenzyl)di-n-propyl-amine hydrochloride | 218–220 |
| 195 | 67 | N-ethylcyclo-hexylamine | N-(3-n-butylamino-4-phenoxy-5-sulfamylbenzyl)-N-ethylcyclo-hexylamine hydrochloride | 164–166 |
| 196 | 67 | 2-ethylamino-ethanol | N-(3-n-butylamino-4-phenoxy-5-sulfamylbenzyl)-N-ethyl-2-hydroxyethylamine hydrochloride hydrate | 156–157 |
| 197 | 67 | 2-isopropyl-aminoethanol | N-(3-n-butylamino-4-phenoxy-5-sulfamylbenzyl)-N-isopropyl-2-hydroxyethylamine hydrochloride hydrate | 150–152 |
| 198 | 67 | 2-diethylamino-ethylamine | (3-n-butylamino-4-phenoxy-5-sulfamylbenzyl)-2-diethyl-aminoethylamine dihydrochloride | 205–206 |
| 199 | 67 | N-benzylmethyl-amine | N-(3-n-butylamino-4-phenoxy-5-sulfamylbenzyl)-N-benzyl-methylamine hydrochloride | 219–220 |
| 200 | 67 | 3-chloro-benzylamine | (3-n-butylamino-4-phenoxy-5-sulfamylbenzyl)-3-chlorobenzyl-amine hydrochloride hydrate | 106–108 |
| 201 | 67 | dibenzylamine | (3-n-butylamino-4-phenoxy-5-sulfamylbenzyl)dibenzylamine hydrochloride | 208–210 |
| 202 | 67 | 3-piperidino-propylamine | (3-n-butylamino-4-phenoxy-5-sulfamylbenzyl)-3-piperidino-propylamine dihydrochloride trihydrate | 138–140 |
| 203 | 71 | diethylamine | (4-phenoxy-3-(2'-pyridylmethyl-amino)-5-sulfamylbenzyl)di-ethylamine dihydrochloride | above 260 |
| 204 | 72 | isopropyl-amine | (4-phenoxy-3-(3'-pyridyl-methylamino)-5-sulfamylben- | |

Table VI-continued

| Ex. No. | Example in which the benzylbromide used is described | Amine used in the reaction | Reaction product | Mp ° C. |
|---|---|---|---|---|
| 205 | 78 | methylamine (40% in water) | zyl)isopropylamine dihydrochloride | above 260 |
| 206 | 82 | n-propylamine | (3-n-butylamino-4-(2'-methylphenylthio)-5-sulfamylbenzyl)methylamine hydrochloride | 210–212 |
| 207 | 87 | crotylamine | (3-n-butylamino-4-(4'-chloroanilino)-5-sulfamylbenzyl)-n-propylamine hydrochloride | 222–224 |
| 208 | 88 | isobutylamine | (4-phenoxy-3-(4'-pyridylethyl-(2)-amino)-5-sulfamylbenzyl)crotylamine dihydrochloride | above 260 |
| 209 | 61 | dimethylamine | (3-benzylamino-4-phenylsulfinyl-5-sulfamylbenzyl)isobutylamine hydrochloride | 210–213 |
| 210 | 54 | veratrylamine | (3-amino-4-benzyl-5-sulfamylbenzyl)dimethylamine dihydrochloride hemihydrate | 216–218 |
| 211 | 57 | benzylamine | (4-benzyl-3-n-butoxy-5-sulfamylbenzl)-3,4-dimethoxybenzylamine hydrochloride hydrate | 161–163 |
| 212 | 58 | isopropylamine | (4-benzyl-3-n-butylthio-5-sulfamylbenzyl)benzylamine hydrochloride | 116–117 |
| 213 | 58 | allylamine | (4-benzyl-3-benzylthio-5-sulfamylbenzyl)isopropylamine hydrochloride | 183–185 |
| 214 | 58 | benzylamine | (4-benzyl-3-benzylthio-5-sulfamylbenzyl)allylamine hydrochloride | 189–191 |
| 215 | 60 | ethylamine | (4-benzyl-3-benzylthio-5-sulfamylbenzyl)benzylamine hydrochloride | 178–180 |
|  |  |  | (4-benzyl-3-(2'-pyridylmethylthio)-5-sulfamylbenzyl)ethylamine dihydrochloride | above 260 |

EXAMPLE 216

(3-n-Butylamino-4-phenoxy-5-sulfamylbenzyl)aniline

A solution of 3-n-butylamino-4-phenoxy-5-sulfamylbenzyl bromide hydrobromide (2.5 g; prepared as described in Example 67) and aniline (10 ml) in methanol (20 ml) is refluxed for 16 hours. After cooling the mixture is diluted with water (about 80 ml); the resulting semi-solid precipitate is washed twice with water, which is decanted, and is then crystallized from aqueous ethanol. After filtration and recrystallization from ethanol, (3-n-butylamino-4-phenoxy-5-sulfamylbenzyl)aniline is obtained with a melting point of 142°–143° C.

EXAMPLES 217 – 230

By following the procedure described in Example 216 but using as starting materials the appropriate 4-$R_1$-3-$R_2$-5-sulfamylbenzyl bromide (or hydrobromide) and amine as defined in Table VII below, the corresponding 4-$R_1$-3-$R_2$-5-sulfamyl N-substituted benzylamines of Table VII are obtained.

Table VII

| Ex. No. | Example in which the benzylbromide used is described | Amine used in the reaction | Reaction product | Mp ° C. |
|---|---|---|---|---|
| 217 | 65 | aniline | (3-allylamino-4-phenoxy-5-sulfamylbenzyl)aniline | 118–119 |
| 218 | 66 | aniline | (4-phenoxy-3-propargylamino-5-sulfamylbenzyl)aniline | 125–126 |
| 219 | 67 | o-toluidine | (3-n-butylamino-4-phenoxy-5-sulfamylbenzyl)-2-methylaniline | 142–144 |
| 220 | 67 | 2,6-dimethylaniline | (3-n-butylamino-4-phenoxy-5-sulfamylbenzyl)-2,6-dimethylaniline | 125–127 |
| 221 | 67 | m-fluoroaniline | (3-n-butylamino-4-phenoxy-5-sulfamylbenzyl)-3-fluoroaniline | 156–158 |
| 222 | 68 | aniline | (3-n-pentylamino-4-phenoxy-5-sulfamylbenzyl)aniline | 142–143 |
| 223 | 70 | aniline | (3-benzylamino-4-phenoxy-5-sulfamylbenzyl)aniline | 134–136 |
| 224 | 74 | aniline | (3-benzylamino-4-(4'-methoxyphenoxy)-5-sulfamylbenzyl)aniline | 170–172 |
| 225 | 77 | aniline | (3-benzylamino-4-phenylthio-5-sulfamylbenzyl)aniline hemihydrate | 68–70 |
| 226 | 81 | aniline | (4-anilino-3-benzylamino-5-sulfamylbenzyl)aniline | 173–175 |
| 227 | 83 | aniline | (3-benzylamino-4-(4'-chloro- | |

Table VII-continued

| Ex. No. | Example in which the benzyl-bromide used is described | Amine used in the reaction | Reaction product | Mp ° C. |
|---|---|---|---|---|
| 228 | 85 | aniline | anilino)-5-sulfamylbenzyl)-aniline (4-benzyl-3-n-butylamino-5-sulfamylbenzyl)aniline hemihydrate | 164–165<br>98–99 |
| 229 | 86 | aniline | (4-benzyl-3-benzylamino-5-sulfamylbenzyl)aniline | 99–101 |
| 230 | 54 | aniline | (4-benzyl-3-n-butoxy-5-sulfamylbenzyl)aniline | 77–80 |

EXAMPLE 231

(3-Allylamino-4-phenoxy-5-sulfamylbenzyl)isopropylamine

A mixture of 3-allylamino-4-phenoxy-5-sulfamylbenzaldehyde (10 g; prepared as described in Example 91), isopropylamine (4.0 ml) and methanol (100 ml) is stirred at 22°–25° C. for 24 hours and is then refluxed for 2 hours. To the stirred solution, sodium borohydride (4.0 g) is added in small portions during about 45 minutes, keeping the temperature at 0°–5° C. by external cooling. After the addition is completed, the reaction mixture is stirred at 0°–5° C. for a further 2 hours, whereafter acetic acid (4 ml) followed by water (300 ml) are cautiously added to precipitate crude (3-allylamino-4-phenoxy-5-sulfamylbenzyl)isopropylamine. After filtration and recrystallization from aqueous ethanol it is obtained with a melting point of 98°–100° C. The material (IR, analysis) is identical with the material prepared as in Example 113.

EXAMPLES 232 – 288

By following the procedure described in Example 231 but using as starting materials the appropriate 4-$R_1$-3-$R_2$-5-sulfamylbenzaldehyde and amine as defined in Table VIII below, the corresponding 4-$R_1$-3-$R_2$-5-sulfamyl N-substituted benzylamines of Table VIII are obtained.

Table VIII

| Ex. No. | Example in which the benzaldehyde used is described | Amine used in the reaction | Reaction product | Mp ° C. |
|---|---|---|---|---|
| 232 | 89 | cyclopentylamine | (3-methylamino-4-phenoxy-5-sulfamylbenzyl)cyclopentylamine hydrate | 88–92 |
| 233 | 90 | sec-butylamine | (3-ethylamino-4-phenoxy-5-sulfamylbenzyl)sec-butylamine dihydrate | 96–98 |
| 234 | 91 | aniline | (3-allylamino-4-phenoxy-5-sulfamylbenzyl)aniline | 117–119 |
| 235 | 92 | isopropylamine | (4-phenoxy-3-propargylamino-5-sulfamylbenzyl)isopropylamine | 155–156 |
| 236 | 92 | aniline | (4-phenoxy-3-propargylamino-5-sulfamylbenzyl)aniline | 125–127 |
| 237 | 93 | isobutylamine | (3-n-butylamino-4-phenoxy-5-sulfamylbenzyl)isobutylamine | 126–127 |
| 238 | 93 | aniline | (3-n-butylamino-4-phenoxy-5-sulfamylbenzyl)aniline | 140–141 |
| 239 | 93 | o-toluidine | (3-n-butylamino-4-phenoxy-5-sulfamylbenzyl)-2-methylaniline | 143–144 |
| 240 | 93 | p-toluidine | (3-n-butylamino-4-phenoxy-5-sulfamylbenzyl)-4-methylaniline, ethanol | 95–97 |
| 241 | 93 | 3,4-dimethylaniline | (3-n-butylamino-4-phenoxy-5-sulfamylbenzyl)-3,4-dimethylaniline | 127–130 |
| 242 | 93 | o-hydroxyaniline | (3-n-butylamino-4-phenoxy-5-sulfamylbenzyl)-2-hydroxyaniline | 107–109 |
| 243 | 93 | m-hydroxyaniline | (3-n-butylamino-4-phenoxy-5-sulfamylbenzyl)-3-hydroxyaniline hydrate | 100–102 |
| 244 | 93 | p-hydroxyaniline | (3-n-butylamino-4-phenoxy-5-sulfamylbenzyl)-4-hydroxyaniline | 173–174 |
| 245 | 93 | o-anisidine | (3-n-butylamino-4-phenoxy-5-sulfamylbenzyl)-2-methoxyaniline | 183–184 |
| 246 | 93 | m-phenetidine | (3-n-butylamino-4-phenoxy-5-sulfamylbenzyl)-3-ethoxyaniline | 161–163 |
| 247 | 93 | o-trifluoromethylaniline | (3-n-butylamino-4-phenoxy-5-sulfamylbenzyl)-2-trifluoromethylaniline | 180–181 |
| 248 | 93 | m-fluoroaniline | (3-n-butylamino-4-phenoxy-5-sulfamylbenzyl)-3-fluoroaniline | 156–157 |

Table VIII-continued

| Ex. No. | Example in which the benzaldehyde used is described | Amine used in the reaction | Reaction product | Mp ° C. |
|---|---|---|---|---|
| 249 | 93 | m-chloroaniline | (3-n-butylamino-4-phenoxy-5-sulfamylbenzyl)-3-chloroaniline | 145–146 |
| 250 | 93 | 4-chloro-2-methylaniline | (3-n-butylamino-4-phenoxy-5-sulfamylbenzyl)-4-chloro-2-methylaniline | 160–162 |
| 251 | 93 | p-bromoaniline | (3-n-butylamino-4-phenoxy-5-sulfamylbenzyl)-4-bromoaniline, ethanol | 146–148 |
| 252 | 93 | 3-aminopyridine | (3-n-butylamino-4-phenoxy-5-sulfamylbenzyl)-3-aminopyridine | 195–196 |
| 253 | 93 | 6-amino-2-methylpyridine | (3-n-butylamino-4-phenoxy-5-sulfamylbenzyl)-6-amino-2-methylpyridine | 136–138 |
| 254 | 94 | isopropylamine | (3-crotylamino-4-phenoxy-5-sulfamylbenzyl)isopropylamine, ethanol | 106–109 |
| 255 | 94 | aniline | (3-crotylamino-4-phenoxy-5-sulfamylbenzyl)aniline | 99–101 |
| 256 | 95 | isopropylamine | (3-n-pentylamino-4-phenoxy-5-sulfamylbenzyl)isopropylamine | 116–117 |
| 257 | 95 | aniline | (3-n-pentylamino-4-phenoxy-5-sulfamylbenzyl)aniline | 142–143 |
| 258 | 96 | isopropylamine | (3-(2'-furfurylamino)-4-phenoxy-5-sulfamylbenzyl)isopropylamine trihydrate | 125–127 |
| 259 | 96 | allylamine | (3-(2'-furfurylamino)-4-phenoxy-5-sulfamylbenzyl)-allylamine acetate | 201–203 (see below) |
| 260 | 96 | benzylamine | (3-(2'-furfurylamino)-4-phenoxy-5-sulfamylbenzyl)-benzylamine acetate | 153–154 (see below) |
| 261 | 96 | aniline | (3-(2'-furfurylamino)-4-phenoxy-5-sulfamylbenzyl)-aniline | 155–156 |
| 262 | 97 | isopropylamine | (4-phenoxy-5-sulfamyl-3-(2'-thenylamino)benzyl)isopropylamine hemihydrate | 113–115 |
| 263 | 97 | allylamine | (4-phenoxy-5-sulfamyl-3-(2'-thenylamino)benzyl)allylamine hemihydrate | 81–83 |
| 264 | 97 | benzylamine | (4-phenoxy-5-sulfamyl-3-(2'-thenylamino)benzyl)benzylamine | 185–187 |
| 265 | 97 | aniline | (4-phenoxy-5-sulfamyl-3-(2'-thenylamino)benzyl)aniline hemihydrate | 95–97 |
| 266 | 98 | isopropylamine | (4-phenoxy-3-(4'-pyridylethyl-(2)-amino)-5-sulfamylbenzyl)isopropylamine dihydrate | 86–90 |
| 267 | 99 | aniline | (3-n-butylamino-4-(4'-methoxyphenoxy)-5-sulfamylbenzyl)aniline hemihydrate | 102–105 |
| 268 | 100 | isopropylamine | (3-benzylamino-4-(4'-methoxyphenoxy)-5-sulfamylbenzyl)isopropylamine | 193–195 |
| 269 | 100 | allylamine | (3-benzylamino-4-(4'-methoxyphenoxy)-5-sulfamylbenzyl)-allylamine | 166–167 |
| 270 | 100 | benzylamine | (3-benzylamino-4-(4'-methoxyphenoxy)-5-sulfamylbenzyl)-benzylamine | 182–183 |
| 271 | 100 | aniline | (3-benzylamino-4-(4'-methoxyphenoxy)-5-sulfamylbenzyl)-aniline | 171–172 |
| 272 | 101 | n-butylamine | (4-benzyl-3-n-butylamino-5-sulfamylbenzyl)-n-butylamine | 139–141 |
| 273 | 101 | aniline | (4-benzyl-3-n-butylamino-5-sulfamylbenzyl)aniline hemihydrate | 98–99 |
| 274 | 102 | allylamine | (4-benzyl-3-(2'-furfurylamino)-5-sulfamylbenzyl)allylamine hydrate | 96–98 |
| 275 | 102 | aniline | (4-benzyl-3-(2'-furfurylamine)-5-sulfamylbenzyl)aniline | 148–150 |
| 276 | 103 | 2-phenethylamine | (4-benzyl-3-methoxy-5-sulfamylbenzyl)-2-phenethylamine hemihydrate | 103–105 |
| 277 | 104 | crotylamine | (4-benzyl-3-ethoxy-5-sulfamylbenzyl)crotylamine dihydrate | 87–90 |
| 278 | 105 | n-propylamine | (4-benzyl-3-n-propoxy-5-sulfamylbenzyl)-n-propylamine hemihydrate | 106–108 |
| 279 | 106 | allylamine | (4-benzyl-3-isopropoxy-5-sulfamylbenzyl)allylamine, sesquihydrate | 94–96 |
| 280 | 107 | isopropyl- | (4-benzyl-3-n-butoxy-5- | |

Table VIII-continued

| Ex. No. | Example in which the benzaldehyde used is described | Amine used in the reaction | Reaction product | Mp ° C. |
|---|---|---|---|---|
| 281 | 107 | amine n-butylamine | sulfamylbenzyl)isopropylamine (4-benzyl-3-n-butoxy-5-sulfamylbenzyl)-n-butylamine | 139–141 121–122 |
| 282 | 107 | veratrylamine | (4-benzyl-3-n-butoxy-5-sulfamylbenzyl)-3,4-dimethoxy-benzylamine hydrochloride | 161–162 (see below) |
| 283 | 107 | aniline | (4-benzyl-3-n-butoxy-5-sulfamylbenzyl)aniline | 79–80 |
| 284 | 108 | 2-phenethyl-amine | (4-benzyl-3-isopentyloxy-5-sulfamylbenzyl)-2-phenethyl-amine hydrate | 82–86 |
| 285 | 109 | isopropyl-amine | (4-benzyl-3-benzyloxy-5-sulfamylbenzyl)isopropylamine acetate | 213–215 (see below) |
| 286 | 109 | allylamine | (4-benzyl-3-benzyloxy-5-sulfamylbenzyl)allylamine | 123–125 |
| 287 | 109 | benzylamine | (4-benzyl-3-benzyloxy-5-sulfamylbenzyl)benzylamine acetate | 144–146 (see below) |
| 288 | 109 | aniline | (4-benzyl-3-benzyloxy-5-sulfamylbenzyl)aniline | 134–136 |

The materials prepared as in Examples 234, 235, 236, 237, 238, 239, 248, 256, 257, 269, 270, 271, 272, 273, 280, 281, 282 and 283 are identical (IR, analysis) with the materials prepared as in Examples 217, 114, 218, 120, 216, 219, 221, 147, 222, 154, 155, 224, 174, 228, 182, 183, 210 and 230 respectively. The compounds of Examples 259, 260, 285 and 287 are isolated as acetates, while the compound of Example 282 is converted to the hydrochloride following the procedure described in Example 191.

EXAMPLE 289

3-n-Butylamino-4-phenoxy-5-sulfamylbenzylamine

To a mixture of lithium aluminium hydride (1.6 g) and dry tetrahydrofuran (10 ml), a solution of 3-n-butylamino-4-phenoxy-5-sulfamylbenzamide (2.25 g) in dry pyridine (20 ml) is added, and the mixture is refluxed for 16 hours. After cooling, ethyl acetate (1 ml) followed by water (6 ml) are very cautiously added dropwise, whereafter the mixture is stirred for a further 30 minutes. It is then heated on a steambath and filtered hot; the filter-cake is carefully washed with hot 2-methoxyethanol (3 portions of 20 ml). The combined filtrates are evaporated in vacuo and the residue is crystallized from ethanol to give 3-n-butylamino-4-phenoxy-5-sulfamylbenzylamine with a melting point of 195°–198° C.

EXAMPLE 290

(3-n-Butylamino-4-phenoxy-5-sulfamylbenzyl)methylamine

By replacing in Example 289 3-n-butylamino-4-phenoxy-5-sulfamylbenzamide with an equimolar amount of 3-n-butylamino-4-phenoxy-5-sulfamyl-N-methylbenzamide and following the procedure described, (3-n-butylamino-4-phenoxy-5-sulfamylbenzyl)-methylamine is obtained with a melting point of 157°–159° C. The material (IR, analysis) is identical with the material prepared as in Example 115.

EXAMPLE 291

(4-Benzyl-3-n-butoxy-5-sulfamylbenzyl)dimethylamine

A. 4-Benzyl-3-n-butoxy-5-sulfamyl-N,N-dimethylbenzamide

A mixture of 4-benzyl-3-n-butoxy-5-sulfamylbenzoic acid (3.6 g), thionyl chloride (20 ml) and N,N-dimethylformamide (0.1 ml) is refluxed for 1 hour and is then evaporated in vacuo. The resulting crude 4-benzyl-3-n-butoxy-5-sulfamylbenzoyl chloride is dissolved in methylene chloride (30 ml), and the resulting solution is during about 15 minutes added dropwise to a stirred mixture of dimethylamine (10 ml; 40% in water) and methylene chloride (20 ml), keeping the temperature at 0°–5° C. by external cooling. After stirring for an additional 2 hours at 22°–25° C., the mixture is washed with water and the organic layer is separated and dried in the presence of magnesium sulphate. Filtration followed by evaporation in vacuo yields crude 4-benzyl-3-n-butoxy-5-sulfamyl-N,N-dimethylbenzamide. After recrystallization from benzene it is obtained with a melting point of 199°–201° C.

B. (4-Benzyl-3-n-butoxy-5-sulfamylbenzyl)dimethylamine

By replacing in Example 289 3-n-butylamino-4-phenoxy-5-sulfamylbenzamide with an equimolar amount of 4-benzyl-3-n-butoxy-5-sulfamyl-N,N-dimethylbenzamide and following the procedure described, (4-benzyl-3-n-butoxy-5-sulfamylbenzyl)dimethylamine is obtained with a melting point of 110°–111° C. The material (IR, analysis) is identical with the material prepared as in Example 180.

EXAMPLE 292

(4-Benzyl-3-n-butoxy-5-sulfamylbenzyl)-2-diethylaminoethylamine

A. 4-Benzyl-3-n-butoxy-5-sulfamyl-N-(2'-diethylaminoethyl)benzamide.

By replacing in Example 291, step A, dimethylamine with an equimolar amount of 2-diethylaminoethylamine and following the procedure described, 4-benzyl-3-n-butoxy-5-sulfamyl-N-(2'-diethylaminoethyl)benzamide is obtained with a melting point of 163° C.

B. (4-Benzyl-3-n-butoxy-5-sulfamylbenzyl)-2-diethylaminoethylamine

By replacing in Example 289 3-n-butylamino-4-phenoxy-5-sulfamylbenzamide with an equimolar amount of 4-benzyl-3-n-butoxy-5-sulfamyl-N-(2'-diethylaminoethyl)-benzamide and following the procedure described, (4-benzyl-3-n-butoxy-5-sulfamylbenzyl)-2-diethylaminoethylamine is obtained as a dihydrate with a melting point of 89°–93° C.

EXAMPLE 293

(4-benzyl-3-n-butoxy-5-sulfamylbenzyl)-3-piperidinopropylamine

A. 4-Benzyl-3-n-butoxy-5-sulfamyl-N-(3'-piperidinopropyl)-benzamide

By replacing in Example 291, step A, dimethylamine with an equimolar amount of 3-piperidinopropylamine and following the procedure described, 4-benzyl-3-n-butoxy-5-sulfamyl-N-(3'-piperidinopropyl)benzamide is obtained with a melting point of 138° C.

B. (4-Benzyl-3-n-butoxy-5-sulfamylbenzyl)-3-piperidinopropylamine

By replacing in Example 289 3-n-butylamino-4-phenoxy-5-sulfamylbenzamide with an equimolar amount of 4-benzyl-3-n-butoxy-5-sulfamyl-N-(3'-piperidinopropyl)benzamide and following the procedure described, (4-benzyl-3-n-butoxy-5-sulfamylbenzyl)-3-piperidinopropylamine is obtained as a hemihydrate with a melting point of 98°–101° C.

EXAMPLE 294

3-n-Butylamino-4-phenoxy-5-sulfamylbenzylamine hydrochloride

A. 3-n-Butylamino-4-phenoxy-5-sulfamylbenzaldoxime

To a solution of 3-n-butylamino-4-phenoxy-5-sulfamylbenzaldehyde (10 g; prepared as in Example 93) in hot methanol (100 ml) a solution of hydroxylamine hydrochloride (10 g) and ammonium acetate (10 g) in water (25 ml) is added, and the mixture is left for 3 days. Water (500 ml) is then added, and the resulting precipitate is collected by filtration, washed with water and dried in air. After recrystallization from a mixture of ethanol and 2-methoxyethanol, 3-n-butylamino-4-phenoxy-5-sulfamylbenzaldoxime is obtained with a melting point of 226°–228° C.

B. 3-n-Butylamino-4-phenoxy-5-sulfamylbenzylamine hydrochloride

A mixture of 3-n-butylamino-4-phenoxy-5-sulfamylbenzaldoxime (3.6 g), stannous chloride dihydrate (12 g), concentrated hydrochloric acid (25 ml) and acetic acid (50 ml) is heated on a steam-bath for 2–3 hours. After concentration in vacuo to about 50 ml, 3-n-butylamino-4-phenoxy-5sulfamylbenzylamine hydrochloride starts to crystallize from the solution. After cooling, the hydrochloride is collected by filtration, washed with ethanol and dried in air. After recrystallization from 2-methoxyethanol it is obtained with a melting point higher than 300° C.

EXAMPLE 295

3-n-Butylamino-4-phenoxy-5-sulfamylbenzylamine

A. 3-n-Butylamino-4-phenoxy-5-sulfamylbenzonitrile

A mixture of 3-n-butylamino-4-phenoxy-5-sulfamylbenzamide (8.5g) and phosphorus oxychloride (25 ml) is heated at 120° C. for 2 hours. The mixture is then evaporated in vacuo and the residue is triturated with icewater (120 ml) to yield crude 3-n-butylamino-4-phenoxy5-sulfamylbenzonitrile. After filtration, carefully washing with water, drying and recrystallization from methanol, it is obtained with a melting point of 217°–218° C.

B. 3-n-Butylamino-4-phenoxy-5-sulfamylbenzylamine

To a stirred mixture of lithium aluminum hydride (5.0 g) and 1,2-dimethoxyethane (100 ml) a solution of 3-n-butylamino-4-phenoxy-5-sulfamylbenzonitrile (15 g) in dry 1,2-dimethoxyethane (150 ml) is during about 1 hour at 100° C. dropwise added, and the mixture is stirred and refluxed for a further 16 hours. After cooling, ethyl acetate (10 ml) followed by water (20 ml) are very cautiously added dropwise, whereafter the mixture is stirred for a further 30 minutes. It is then heated on a steam-bath and filtered hot; the filter-cake is carefully washed with hot 2-methoxyethanol (3 portions of 50 ml). The combined filtrates are evaporated in vacuo to yield crude 3-n-butylamino-4-phenoxy-5-sulfamylbenzylamine. After recrystallization from 2-methoxyethanol it is obtained with a melting point of 197°–198° C. The material (IR, analysis) is identical with the material prepared as in Example 289.

EXAMPLE 296

3-n-Butylamino-4-phenoxy-5-sulfamylbenzylamine formate hemihydrate.

To a solution of (3-n-butylamino-4-phenoxy-5-sulfamyl-benzyl)benzylamine (8.8 g; prepared as described in Example 136) in 2-methoxyethanol (90 ml), palladium (10%) on carbon (4.0 g) is added and the mixture is hydrogenated. After about 5 hours the theoretical amount of hydrogen has been absorbed, and the mixture is heated on a steam-bath and filtered to remove the catalyst. The filtrate is evaporated in vacuo and the residue triturated with water to yield crude 3-n-butylamino-4-phenoxy-5-sulfamylbenzylamine. The crude amine is dissolved in formic acid (50 ml), whereafter the solution is evaporated in vacuo. The residue is recrystallized from a mixture of ethanol and 2-methoxyethanol to yield, after filtration and drying, 3-n-butylamino-4-phenoxy-5-sulfamylbenzylamine formate hemihydrate with a melting point of 224°–226° C.

EXAMPLE 297

4-Benzyl-3-n-butoxy-5-sulfamylbenzylamine hydrochloride hydrate

By replacing in Example 296 (3-n-butylamino-4-phenoxy-5-sulfamylbenzyl)benzylamine with an equimolar amount of (4-benzyl-3-n-butoxy-5-sulfamylbenzyl)benzylamine (prepared as described in Example 184) and following the hydrogenation procedure described, crude 4-benzyl-3-n-butoxy-5-sulfamylbenzylamine is obtained. The crude amine is dissolved in ethanol (50 ml) and a saturated solution of dry hydrogen chloride in ethanol (2 ml) is added to precipitate, after cooling, 4-benzyl-3-n-butoxy-5-sulfamylbenzylamine hydrochloride. After filtration and recrystallization from ethanol it is obtained as a hydrate with a melting point of 176°–179° C.

EXAMPLE 298

(3-n-Butylamino-4-phenoxy-5-sulfamylbenzyl)-n-butylmethylamine

To a stirred mixture of (3-n-butylamino-4-phenoxy-5-sulfamylbenzyl)methylamine (3.6 g; prepared as described in Example 115), sodium hydrogen carbonate (0.9 g) and hexamethylphosphoric triamide (15ml) a solution of n-butyl iodide (1.85 g) in hexamethylphosphoric triamide (5 ml) is dropwise added during about 1 hour. After additional stirring for 30 minutes, the mixture is diluted with water to precipitate crude (3-n-butylamino-4-phenoxy-5-sulfamylbenzyl)-n-butylmethylamine. After filtration and recrystallization twice from ethanol it is obtained with a melting point of 103°-104° C. The material (IR, analysis) is identical with the material prepared as in Example 128.

EXAMPLES 299 – 302

By following the procedure described in Example 298 but using as starting materials equimolar amounts of the appropriate 4-$R_1$-3-$R_2$-5-sulfamyl N-substituted benzylamine and alkyl halogenide as defined in Table IX below, the corresponding 4-$R_1$-3-$R_2$ -5-sulfamyl N,N-disubstituted benzylamines of Table IX are obtained.

Table IX

| Ex. No. | Example in which the benzylamine used is described | Alkyl halogenide used in the reaction | Reaction product | Mp ° C. |
|---|---|---|---|---|
| 299 | 116 | ethyl iodide | (3-n-butylamino-4-phenoxy-5-sulfamylbenzyl)diethylamine | 116–117 |
| 300 | 117 | n-propyl iodide | (3-n-butylamino-4-phenoxy-5-sulfamylbenzyl)di-n-propylamine hydrochloride | 218–219 (see below) |
| 301 | 129 | isopropyliodide | N-(3-n-butylamino-4-phenoxy-5-sulfamylbenzyl)-N-iso-propyl-2-hydroxyethylamine hydrochloride hydrate | 150–152 (see below) |
| 302 | 115 | benzyl bromide | N-(3-n-butylamino-4-phenoxy-5-sulfamylbenzyl)-N-benzyl-methylamine hydrochloride | 218–220 (see below) |

The materials prepared as in Examples 299, 300, 301 and 302 are identical (IR, analysis) with the materials prepared as in Examples 127, 194, 197 and 199 respectively.

The compounds of Examples 300, 301 and 302 are converted to the hydrochlorides according to the method described in Example 191.

EXAMPLE 303

(3-n-Butylamino-4-phenoxy-5-sulfamylbenzyl)-3-hydroxybenzylamine.

A solution of 3-n-butylamino-4-phenoxy-5-sulfamylbenzylamine (1.05 g; prepared as described in Example 289) and m-hydroxybenzaldehyde (0.45 g) in methanol (7 ml) is refluxed for 16 hours. The resulting solution is cooled to 0°-5° C. whereafter sodium borohydride (0.25 g) is added in portions during 5 minutes while stirring. After stirring at 22°-25° C. for a further 3 hours, acetic acid (0.5 ml) followed by water (20 ml) are added to precipitate crude (3-n-butylamino-4-phenoxy-5-sulfamylbenzyl)-3-hydroxybenzylamine. After filtration and recrystallization from ethanol, it is obtained with a melting point of 174°-175° C.

EXAMPLES 304 – 311

By following the procedure described in Example 303 but using as starting materials equimolar amounts of the appropriate 4-$R_1$-3-$R_2$-5-sulfamylbenzylamine and aldehyde as defined in Table X below, the corresponding 4-$R_1$-3-$R_2$-5-sulfamyl N-substituted benzylamines of Table X are obtained.

Table X

| Ex. No. | Example in which the benzylamine used is described | Aldehyde used in the reaction | Reaction product | Mp ° C. |
|---|---|---|---|---|
| 304 | 289 | benzaldehyde | (3-n-butylamino-4-phenoxy-5-sulfamylbenzyl)benzylamine | 86–87 |
| 305 | 289 | p-methylbenzaldehyde | (3-n-butylamino-4-phenoxy-5-sulfamylbenzyl)-4-methyl-benzylamine | 64–66 |
| 306 | 289 | p-methoxybenzaldehyde | (3-n-butylamino-4-phenoxy-5-sulfamylbenzyl)-4-methoxy-benzylamine hydrate | 77–78 |
| 307 | 289 | furfural | (3-n-butylamino-4-phenoxy-5-sulfamylbenzyl)-2-furfurylamine | 103–105 |
| 308 | 289 | pyridine-3-aldehyde | (3-n-butylamino-4-phenoxy-5-sulfamylbenzyl)-3-picolylamine dihydrochloride hemihydrate | 263–265 (see below) |
| 309 | 289 | pyridine-4-aldehyde | (3-n-butylamino-4-phenoxy-5-sulfamylbenzyl)-4-picolylamine | 193–194 |
| 310 | 297 | benzaldehyde | (4-benzyl-3-n-butoxy-5-sulfamylbenzyl)benzylamine | 86–87 |
| 311 | 297 | veratraldehyde | (4-benzyl-3-n-butoxy-5-sulfamylbenzyl)-3,4-dimethoxy-benzylamine hydrochloride hydrate | 162–163 (see below) |

The materials prepared as in Examples 304, 306, 307, 310 and 311 are identical (IR, analysis) with the materials prepared as in Examples 136, 138, 142, 184 and 210 respectively.

The compounds of Examples 308 and 311 are converted to the hydrochlorides according to the procedure described in Example 191.

EXAMPLE 312

N-(3-n-Butylamino-4-phenoxy-5-sulfamylbenzyl)acetamide

To a solution of 3n-butylamine-4-phenoxy-5-sulfamylbenzylamine (1.05 g; prepared as described in Example 289) in acetic acid (10 ml), acetic anhydride (0.4 ml) is added and the mixture is left for 24 hours.

Dilution with water (25 ml) precipitates N-(3-n-butylamino-4-phenoxy-5-sulfamylbenzyl)acetamide, which is collected by filtration, washed with water and dried in air. After recrystallization from aqueous ethanol it is obtained with a melting point of 190°–191° C.

EXAMPLE 313

N-(3-n-Butylamino-4-phenoxy-5-sulfamylbenzyl)urethan

To a stirred solution of 3-n-butylamino-4-phenoxy-5-sulfamylbenzylamine (1.05 g; prepared as described in Example 289) in pyridine (7ml) ethyl chloroformate (0.3 ml) is dropwise added at 22°–25° C., and the mixture is stirred for a further 1.5 hours. The mixture is then diluted with water (30 ml) and acetic acid (10 ml) to precipitate crude N-(3-n-butylamino-4-phenoxy-5-sulfamylbenzyl)urethan. After filtration and recrystallization from ethanol it is obtained with a melting point of 105°–107° C.

EXAMPLE 314

N-Benzyl-N-(3-n-butylamino-4-phenoxy-5-sulfamylbenzyl)-acetamide

To a solution of (3-n-butylamino-4-phenoxy-5-sulfamylbenzyl)benzylamine (1.1 g; prepared as described in Example 136) in pyridine (6 ml), acetic anhydride (0.26 ml) is added and the mixture is left for 3 hours. Water (25 ml) is then added followed by concentrated hydrochloric acid (3 ml) to precipitate a semi-solid material. After recrystallization twice from aqueous ethanol, N-benzyl-N-(3-n-butylamino-4-phenoxy-5-sulfamylbenzyl)acetamide is obtained with a melting point of 75°–77° C.

EXAMPLE 315

N-Benzyl-N-(3-n-butylamino-4-phenoxy-5-sulfamylbenzyl)-isobutyrylamide

By replacing in Example 314 acetic anhydride with an equimolar amount of isobutyric anhydride and following the procedure described, N-benzyl-N-(3-n-butylamino-4-phenoxy-5-sulfamylbenzyl)-isobutyrylamide is obtained with a melting point of 118°–120° C.

EXAMPLE 316

N-Benzyl-N-(3-n-butylamino-4-phenoxy-5-sulfamylbenzyl)-benzamide

By replacing in Example 314 acetic anhydride with an equimolar amount of benzoyl chloride and following the procedure described, N-benzyl-N-(3-n-butylamino-4-phenoxy-5-sulfamylbenzyl)benzamide is obtained with a melting point of 137°–138° C.

EXAMPLE 317

N-Benzyl-N-(3-n-butylamino-4-phenoxy-5-sulfamylbenzyl)-urethan

By replacing in Example 314 acetic anhydride with an equimolar amount of ethyl chloroformate and following the procedure described, N-benzyl-N-(3-n-butylamino-4-phenoxy-5-sulfamylbenzyl)urethan is obtained with a melting point of 82°–83° C.

EXAMPLES 318–320

By replacing in Example 289 3-n-butylamino-4-phenoxy-5-sulfamylbenzamide with equimolar amounts of the amides defined in Table XI below and following the procedure described, the 4-$R_1$-3-$R_2$-5-sulfamyl N-substituted benzylamines of Table XI are obtained.

Table XI

| Ex. No. | Example in which the amide used is described | Reaction product | Mp ° C. |
|---|---|---|---|
| 318 | 312 | (3-n-butylamino-4-phenoxy-5-sulfamylbenzyl)ethylamine | 152–153 |
| 319 | 314 | N-(3-n-butylamino-4-phenoxy-5-sulfamylbenzyl)-N-benzylethylamine hydrate | 86–89 |
| 320 | 316 | (3-n-butylamino-4-phenoxy-5-sulfamylbenzyl)dibenzylamine hydrochloride | 207–210 (see below) |

The materials prepared as in Examples 318 and 320 are identical (IR, analysis) with the materials prepared as in Examples 116 and 201 respectively. The compound of Example 320 is converted to the hydrochloride according to the procedure described in Example 191.

EXAMPLE 321

(4-Benzyl-3-n-butoxy-5-sulfamylbenzyl)dimethylamine

A. 5-Amino-4-benzyl-3-n-butoxybenzyl alcohol

By replacing in Example 4 methyl 3-amino-4-benzyl-5-sulfamylbenzoate with an equimolar amount of methyl 5-amino-4-benzyl-3-n-butoxybenzoate (mp 82°–83° C.) and following the procedure described, 5-amino-4-benzyl-3-n-butoxybenzyl alcohol is obtained with a melting point of 105°–107° C.

B. 5-Amino-4-benzyl-3-n-butoxybenzyl bromide hydrobromide

By replacing in Example 61 3-amino-4-benzyl-5-sulfamylbenzyl alcohol with 5-amino-3-n-butoxybenzyl alcohol and following the procedure described, 5-amino-4-benzyl-3-n-butoxybenzyl bromide hydrobromide is obtained with a melting point of 159°–162° C.

C. (5-Amino-4-benzyl-3-n-butoxybenzyl)dimethylamine

By replacing in Example 110 3-amino-4-benzyl-5-sulfamylbenzylbromide hydrobromide and n-butylamine with 5-amino-4-benzyl-3-n-butoxybenzyl bromide hydrobromide and dimethylamine (40% in water) respectively, and following the procedure described, (5-amino-4-benzyl-3-n-butoxybenzyl)dimethylamine is obtained as a semi-solid material.

D. (4-Benzyl-3-n-butoxy-5-sulfamylbenzyl)dimethylamine

To a stirred solution of (5-amino-4-benzyl-3-n-butoxybenzyl)dimethylamine (6.25 g) in a mixture of concentrated hydrochloric acid (10 ml) and acetic acid (10 ml) a solution of sodium nitrite (1.4 g) in water (5 ml) is dropwise added during 30 minutes, keeping the temperature at 0°–3° C. by external cooling. After additional stirring at 0° C. for 10 minutes, the resulting diazonium-solution is slowly added to a solution of cupric chloride dihydrate (1.5 g) in water (4 ml) and acetic acid (25 ml) saturated with dry sulphur dioxide while stirring at 22°–25° C. After stirring for a further 1 hour, the mixture is cooled to precipitate crude (4-benzyl-3-n-butoxy-5-chlorosulfonylbenzyl)dimethylamine hydrochloride. The hydrochloride is collected by filtration and washed with a minor amount of ice-cold acetic acid. It is then added in portions to a stirred, saturated solution of dry ammonia in methanol (30 ml) keeping the temperature at 10°–12° C. by external cooling. The resulting solution is stirred for 16 hours at 22°–25° C. and is then diluted with water (100 ml) to precipitate crude (4-benzyl-3-n-butoxy-5-sulfamylbenzyl)dimethylamine. After filtration and recrystallization twice from aqueous ethanol it is obtained with a melting point of 109°–111° C. The material (IR, analysis) is identical with the material prepared as in Example 180.

EXAMPLE 322

(4-Benzyl-3-n-butylamine-5-sulfamylbenzyl)dimethylamine

A mixture of (3-amino-4-benzyl-5-sulfamylbenzyl)-dimethylamine dihydrochloride hemihydrate (4.0 g; dried in vacuo at 78° C. for 16 hours; prepared as described in Example 209), n-butyl iodide (1.9 g), sodium hydrogen carbonate (5.0 g) and hexamethylphosphoric triamide (20 ml) is stirred at 22°–25° C. for 24 hours, and is then diluted with water (200 ml) to precipitate crude (4-benzyl-3-n-butylamino-5-sulfamylbenzyl)dimethylamine. After filtration and recrystallization from ethanol it is obtained with a melting point of 111°–113° C. The material (IR, analysis) is identical with the material prepared as in Example 172.

EXAMPLE 323

(4-Benzyl-3-benzylamino-5-sulfamylbenzyl)dimethylamine

By replacing in Example 322 n-butyl iodide with an equimolar amount of benzyl bromide and following the procedure described, (4-benzyl-3-benzylamino-5-sulfamylbenzyl)dimethylamine is obtained with a melting point of 79°–80° C. The material (IR, analysis) is identical with the material prepared as in Example 176.

EXAMPLE 324

(3-Benzylamino-4-phenoxy-5-sulfamylbenzyl)allylamine

A solution of (3-amino-4-phenoxy-5-sulfamylbenzyl)-allylamine hydrate (3.3 g; prepared as described in Example 111) and benzaldehyde (1.2 g) in methanol (35 ml) is refluxed for 16 hours. Sodium borohydride (1.0 g) is then during 30 minutes added in portions while stirring at 0°–5° C. After additional stirring for 2 hours, acetic acid (1.0 ml) followed by water (120 ml) is cautiously added to precipitate crude (3-benzylamino-4-phenoxy-5-sulfamylbenzyl)allylamine. After filtration and recrystallization twice from aqueous ethanol, it is obtained with a melting point of 139°–140° C. The material (IR, analysis) is identical with the material prepared as in Example 150.

EXAMPLES 325 – 330

By following the procedure described in Example 324 but using as starting materials equimolar amounts of the appropriate 3-amino-4-$R_1$-5-sulfamyl N-substituted benzylamine and aldehyde as defined in Table XII below, the corresponding 4-$R_1$-3-$R_2$-5-sulfamyl N-substituted benzylamines of Table XII are obtained.

Table XII

| Ex. No. | Example in which the benzylamine used is described | Aldehyde used in the reaction | Reaction product | Mp ° C. |
|---|---|---|---|---|
| 325 | 111 | furfural | (3-(2'-furfurylamino)-4-phenoxy-5-sulfamylbenzyl)-allylamine acetate | 200–202 (see below) |
| 326 | 111 | 2-thenaldehyde | (4-phenoxy-5-sulfamyl-3-(2'-thenylamino)benzyl)allylamine hemihydrate | 81–83 |
| 327 | 111 | 3-thenaldehyde | (4-phenoxy-5-sulfamyl-3-(3'-thenylamino)benzyl)allylamine hydrate | 85–87 |
| 328 | 110 | benzaldehyde | (4-benzyl-3-benzylamino-5-sulfamylbenzyl)-n-butylamine | 138–140 |
| 329 | 209 | benzaldehyde | (4-benzyl-3-benzylamino-5-sulfamylbenzyl)dimethylamine hydrate | 79–80 |
| 330 | 170 | benzaldehyde | (4-benzyl-3-benzylamino-5-sulfamylbenzyl)benzylamine | 140–141 |

The materials prepared as in Examples 325, 326, 328, 329 and 330 are identical (IR, analysis) with the materials prepared as in Examples 259, 263, 178, 176 and 179 respectively. The compound of Example 325 is isolated as the acetate.

EXAMPLE 331

(4-Benzyl-3-n-butylamino-5-sulfamylbenzyl)dimethylamine

To a vigorously stirred mixture of (3-amino-4-benzyl-5-sulfamylbenzyl)dimethylamine dihydrochloride hemihydrate (4.0 g; prepared as described in Example 209), 2 N sodium hydroxide (60 ml) and methylene chloride (40 ml) a solution of n-butyryl chloride (1.1 g) in methylene chloride (12 ml) is dropwise added during 30 minutes keeping the temperature at 0°–5° C. by external cooling. After additional stirring at 22°–25° C. for 2 hours, the organic layer is separated, washed with water and dried in the presence of magnesium sulphate. The methylene chloride is then removed in vacuo to yield crude (4-benzyl-3-n-butyrylamido-5-sulfamylbenzyl)-dimethylamine as an oil. The crude amine is dissolved in dry 1,2-dimethoxyethane (50 ml) and the resulting solution is dropwise added at 100° C. during 45 minutes to a stirred mixture of lithium aluminium hydride (2.0 g) and 1,2-dimethoxyethane (40 ml). After additional refluxing and stirring for 16 hours, the mixture is cooled, and ethyl acetate (4 ml) followed by water (8 ml) are very cautiously added. The mixture is stirred for a further 30 minutes and is then heated on a steam-bath and filtered hot. The filtercake is carefully washed with hot 1,2-dimethoxyethane (3 portions of 25 ml), whereafter the combined filtrates are evaporated in vacuo to yield crude (4-benzyl-3-n-butylamino-5-sulfamylbenzyl)dimethylamine. After recrystallization from ethanol it is obtained with a melting point of 111°–113° C. The material (IR, analysis) is identical with the material prepared as in Example 172.

EXAMPLE 332

(4-Benzyl-3-benzylamino-5-sulfamylbenzyl)dimethylamine

By replacing in Example 331 n-butyryl chloride with an equimolar amount of benzoyl chloride and following the procedure described, (4-benzyl-3-benzylamino-5-sulfamylbenzyl)dimethylamine is obtained as a hydrate with a melting point of 78°–80° C. The material (IR, analysis) is identical with the material prepared as in Example 176.

What we claim is:

1. A compound of the formula I

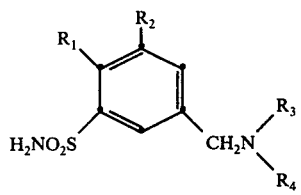

in which
- $R_1$ stands for an unsubstituted or substituted phenoxy or phenylthio radical;
- $R_2$ stands for a $-YR_2'$ radical, in which Y represents $-O-$, $-S-$, or $-NH-$, and $R_2'$, which may be unsubstituted or substituted, represents $C_1-C_6$-alkyl, $C_2-C_6$-alkenyl or -alkynyl; or methyl or ethyl substituted with phenyl radical;
- $R_3$ and $R_4$ which can be the same or different, and unsubstituted or substituted, stand for hydrogen or for a straight or branched $C_1-C_8$-alkyl, $C_2-C_8$-alkenyl or -alkynyl radical, a $C_5-C_7$-cycloalkyl or a phenyl radical, or for a $C_1-C_3$ alkyl radical substituted with phenyl; and
- $R_4$ furthermore stands for a lower carbalkoxy radical, a $C_1-C_6$ alkanoyl radical, or a benzoyl radical; and salts thereof with pharmaceutically acceptable acids wherein when substituted the substituents of $R_1$, $R_2'$, $R_3$, and $R_4$ are selected from the group consisting of halogen atoms, lower alkyl, halo-lower alkyl, nitro and amino groups, mono- or dialkylamino or acylamino groups, hydroxy groups, hydroxy groups, lower alkoxy groups or hydroxy groups esterified with lower aliphatic carboxylic acids, and lower alkylthio or phenylthio radicals.

2. A salt of a compound of formula I of claim 1 with a pharmaceutically acceptable acid selected from the group consisting of hydrochloric and hydrobromic acid, phosphoric acid, nitric acid, p-toluenesulfonic acid, methanesulfonic acid, formic acid, acetic acid, propionic acid, citric acid, tartaric acid and maleic acid.

3. A compound of formula I of claim 1 in which $R_1$ stands for phenoxy or phenylthio radical; Y stands for $-NH-$; and $R_2'$, $R_3$ and $R_4$ have the meanings defined in claim 1.

4. A compound of formula I of claim 1 in which $R_1$ stands for phenoxy or phenylthio radical; Y stands for $-S-$; and $R_2'$, $R_3$ and $R_4$ have the meanings defined in claim 1.

5. A compound of formula I of claim 1 in which $R_1$ stands for aniline radical; Y stands for $-NH-$; and $R_2'$, $R_3$ and $R_4$ have the meanings defined in claim 1.

6. A compound of formula I of claim 1 in which $R_1$ stands for benzyl radical; Y stands for $-NH-$; and $R_2'$, $R_3$ and $R_4$ have the meanings defined in claim 1.

7. A compound of formula I of claim 1 in which $R_1$ stands for benzyl radical; Y stands for $-O-$ or $-S-$; and $R_2'$, $R_3$ and $R_4$ have the meanings defined in claim 1.

8. A compound of formula I of claim 1, in which $R_3$ and $R_4$ each represents hydrogen, $C_1-C_8$ alkyl, $C_3-C_5$-alkenyl, $C_5-C_7$-cycloalkyl or phenyl or $R_3$ and $R_4$ each represents $C_1-C_3$ alkyl substituted with one or two phenyl radicals or $R_4$ represents carbethoxy, $C_2-C_4$ alkanoyl or benzoyl.

9. A compound of formula I of claim 1, in which $R_2'$ when representing an alkenyl or alkynyl radical, stands for a radical with three to five carbon atoms.

10. 3-n-butylamino-4-phenoxy-5-sulfamylbenzylamine hydrochloride.

11. (3-n-butylamino-4-phenoxy-5-sulfamylbenzyl)aniline.

12. (3-n-butylamino-4-phenoxy-5-sulfamylbenzyl)allylamine.

13. (3-n-butylamino-4-phenylthio-5-sulfamylbenzyl)isopropylamine.

14. (4-anilino-3-benzylamino-5-sulfamylbenzyl)aniline.

15. (4-benzyl-3-benzyloxy-5-sulfamylbenzyl)aniline.

16. (4-benzyl-3-n-butylthio-5-sulfamylbenzyl)allylamine.

17. (4-benzyl-3-n-butoxy-5-sulfamylbenzyl)aniline.

18. A compound of formula III

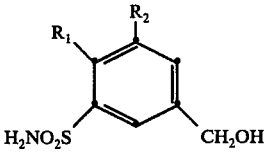

in which $R_1$ stands for an unsubstituted or substituted phenoxy or phenylthio radical;
- $R_2$ stands for a $-YR_2'$ radical, in which Y represents $-NH-$, and $R_2'$, which may be unsubstituted or substituted, represents $C_1-C_6$-alkyl, $C_2-C_6$-alkenyl or -alkynyl; or methyl or ethyl substituted with a phenyl radical;
- wherein when substituted the substitutuents of $R_1$ and $R_2'$ are selected from the group consisting of halogen atoms, lower alkyl, halo-lower alkyl, nitro and amino groups, mono- or dialkylamino or acylamino groups, hydroxy groups, lower alkoxy groups or hydroxy groups esterified with lower aliphatic carboxylic acids, and lower alkylthio or phenylthio radicals.

19. A compound of the formula I

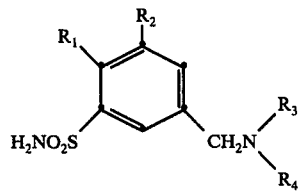

in which
- $R_1$ stands for a phenoxy, phenylthio or benzyl radical;
- $R_2$ stands for a $-YR_2'$ radical, in which Y represents $-O-$, $-S-$, or $-NH-$, and $R_2'$, represents $C_1$-

$C_6$-alkyl, $C_2$-$C_6$-alkenyl or -alkynyl; or methyl or ethyl substituted with phenyl radical;

$R_3$ and $R_4$ which can be the same or different, stand for hydrogen or for a straight or branched $C_1$-$C_8$-alkyl, $C_2$-$C_8$-alkenyl or -alkynyl radical, a $C_5$-$C_7$-cycloalkyl or a phenyl radical, or for a $C_1$-$C_3$ alkyl radical substituted with phenyl; and $R_4$ furthermore stands for a lower carbalkoxy radical, a $C_1$-$C_6$ alkanoyl radical, or a benzoyl radical; and salts thereof with pharmaceutically acceptable acids.

20. A compound according to claim 19 wherein $R_1$ is a phenoxy radical; $R_2$ is —$NHR_2'$ wherein $R_2'$ is $C_1$-$C_6$ alkyl; and $R_3$ and $R_4$ are hydrogen, $C_1$-$C_8$ alkyl or $C_2$-$C_8$ alkenyl.

21. A pharmaceutical preparation in dosage unit form for the enteral or parenteral treatment of patients suffering from hypertension or oedemas, which comprises as an active ingredient a compound according to claim 1 of formula I, or a salt thereof with a pharmaceutically acceptable acid, and an atoxic pharmaceutically acceptable carrier, the quantity of the said active compound being between 0.1 and 50 mg.

22. A preparation as claimed in claim 21 wherein the dosage unit contains from 0.25 to 25 mg of a compound of formula I or a salt thereof with a pharmaceutically acceptable inorganic or organic acid.

23. A preparation as claimed in claim 21 wherein the dosage unit is in the form of a tablet.

24. A preparation as claimed in claim 21 wherein the dosage unit is in the form of a capsule.

25. An injectable pharmaceutical preparation for the treatment of patients suffering from hypertension or oedemas in dosage unit form, containing from 0.1 mg to 50 mg of a compound of formula I of claim 1 or a salt thereof with a pharmaceutically acceptable acid, dissolved in an aqueous medium.

26. A preparation according to claim 25, dissolved or suspended in a non-toxic, pharmaceutically acceptable vehicle.

27. A pharmaceutical preparation for oral treatment of patients suffering from hypertension or oedemas in form of a sustained-release preparation in dosage unit form of a compound of claim 1, in which the dose of the active compound is between 0.1 to 50 mg.

28. A method of treating patients suffering from oedematous conditions and from hypertension, comprising administering to adult patients from 0.25 to 100 mg per day of a compound of formula I of claim 1 or an equivalent amount of a salt thereof as defined in claim 1.

* * * * *